United States Patent
Kessler et al.

(10) Patent No.: US 11,332,498 B2
(45) Date of Patent: May 17, 2022

(54) LIGANDS FOR INTEGRIN αVβ8, SYNTHESIS AND USES THEREOF

(71) Applicant: Technische Universitat Munchen, Munich (DE)

(72) Inventors: Horst Kessler, Schwalbach (DE); Tobias Kapp, Lörrach (DE); Florian Reichart, Munich (DE); Oleg Maltsev, Kufstein (AT)

(73) Assignee: Technische Universitat Munchen, Munich (DE)

( * ) Notice: Subject to any disclaimer, the term of this patent is extended or adjusted under 35 U.S.C. 154(b) by 0 days.

(21) Appl. No.: 16/494,467

(22) PCT Filed: Mar. 16, 2018

(86) PCT No.: PCT/EP2018/056733
§ 371 (c)(1),
(2) Date: Sep. 16, 2019

(87) PCT Pub. No.: WO2018/167295
PCT Pub. Date: Sep. 20, 2018

(65) Prior Publication Data
US 2020/0087347 A1    Mar. 19, 2020

(30) Foreign Application Priority Data
Mar. 17, 2017    (EP) ..................... 17161590

(51) Int. Cl.
| | | |
|---|---|---|
| *C07K 7/64* | (2006.01) |
| *A61K 47/64* | (2017.01) |
| *A61K 38/00* | (2006.01) |
| *G01N 33/68* | (2006.01) |
| *A61K 49/00* | (2006.01) |

(52) U.S. Cl.
CPC .............. *C07K 7/64* (2013.01); *A61K 47/64* (2017.08); *A61K 49/0002* (2013.01); *G01N 33/68* (2013.01); *A61K 38/00* (2013.01)

(58) Field of Classification Search
None
See application file for complete search history.

(56) References Cited

U.S. PATENT DOCUMENTS

2006/0029544 A1    2/2006  Sutcliffe-Goulden et al.

FOREIGN PATENT DOCUMENTS

| EP | 1077218 A2 | 2/2001 |
|---|---|---|
| WO | WO 2011/079015 A1 | 6/2011 |
| WO | WO 2012/007137 A1 | 1/2012 |
| WO | WO 2016/029131 A1 | 2/2016 |
| WO | WO 2016/046225 A1 | 3/2016 |
| WO | WO 2016/067010 * | 5/2016 |

OTHER PUBLICATIONS

Gagnon et al. (PNAS Oct. 20, 2009 106 (42) 17904-17909) (Year: 2009).*
Kelly et al., J. Exp. Med. 2018, vol. 215, No. 11, 2725-2736 (Year: 2018).*
International Search Report and Written Opinion dated May 23, 2018 in connection with International Application No. PCT/EP2018/056733.
International Preliminary Report on Patentability dated Sep. 17, 2019 in connection with International Application No. PCT/EP2018/056733.
Bochen et al., Biselectivity of isoDGR peptides for fibronectin binding integrin subtypes α5β1 and αvβ6: conformational control through flanking aino acids. J Med Chem. Feb. 28, 2013;56(4):1509-19. doi: 10.1021/jm301221x. Epub Feb. 18, 2013.
Hovlid et al., Guiding plant virus particles to integrin-displaying cells. Nanoscale. Jun. 21, 2012;4(12):3698-705. doi: 10.1039/c2nr30571b. Epub May 15, 2012.

(Continued)

*Primary Examiner* — Sergio Coffa
(74) *Attorney, Agent, or Firm* — Wolf, Greenfield & Sacks, P.C.

(57) ABSTRACT

Disclosed are compounds represented by the following general formula (I): Cyclo-(Arg-Gly-Asp-$X^1$-$X^2$-$X^3$-$X^4$-$X^5$) (I) wherein the variables groups $X^1$ to $X^5$ have the following meanings $X^1$: Leu, Ile, Nle, Val, Tyr, Phe; $X^2$: D-amino acid such as D-Pro, N-Me-D-Phe; $X^3$: Pro, N-Me-amino acid such as N-Me-Lys, N-Me-Lys(Ac); Pro-Rx3, N-Me-Lys-Rx4; $X^4$: Gly, Ala, Ser, Thr; $X^5$: Leu, Ala, Tyr, His, Ile, Nle, Val, Phe wherein Pro-Rx3 represents a proline residue that carries at the C-3, C-4 or C-5 carbon atom and preferably the C-4 carbon atom a functional group selected from —NH2, —OH, —NH—Ac, —NH-hexyne, and wherein Lys-$R^{x4}$ represents a lysine residue, wherein the ω-amino nitrogen atom carries a group of the formula -L4-R4, wherein L4 is selected from the group consisting of covalent bond, —C(O)—, and —C(O)—O—, . . . , and wherein R4 is selected from the group consisting of —(CH2)n-C≡CH with n=0, 1, 2, 3, 4, 5, 6, 7 or 8, or wherein the sub-sequence -$X^2$-$X^3$- represents a β-turn mimetic diffeωωring from the meanings above, or pharmaceutically acceptable salts, esters, solvates, polymorphs or modified forms thereof represented by the following general formula (II): $(X^0)_{n1}$L$(X^8)_{n2}$ wherein X0 represents the compound of the general formula (I) as specified above (excluding one hydrogen atom to allow bonding to the linker), L represents a linker, $X^8$ represents the effector moiety and wherein n1 and n2 are each independently selected from the range of 1 to 5, preferably such that each of n1 and n2 represents 1, wherein n1+n2 represents the number of valencies of the linker and is preferably in the range of from 2 to 6, more preferably 2-5, with the proviso that each of n1 and n2 is at least 1, as well as uses therefore in therapy and imaging.

24 Claims, No Drawings
Specification includes a Sequence Listing.

(56) References Cited

OTHER PUBLICATIONS

Hsiao et al., Cyclic alphavbeta6-targeting peptide selected from biopanning with clinical potential for head and neck squamous cell carcinoma. Head Neck. Feb. 2010;32(2):160-72. doi: 10.1002/hed. 21166.

Kapp et al., A Comprehensive Evaluation of the Activity and Selectivity Profile of Ligands for RGD-binding Integrins. Sci Rep. Jan. 11, 2017;7:39805. doi: 10.1038/srep39805.

Kapp et al., Integrin modulators: a patent review. Expert Opin Ther Pat. Oct. 2013;23(10):1273-95. doi: 10.1517/13543776.2013. 818133. Review.

Kraft et al., Definition of an unexpected ligand recognition motif for alphav beta6 integrin. J Biol Chem. Jan. 22, 1999;274(4):1979-85.

Li et al., Synthesis and biological evaluation of a peptide-paclitaxel conjugate which targets the integrin $\alpha v\beta_6$. Bioorg Med Chem. Sep. 15, 2011;19(18):5480-9. doi: 10.1016/j.bmc.2011.07.046. Epub Aug. 4, 2011.

Ley et al., Integrin-based therapeutics: biological basis, clinical use and new drugs. Nat Rev Drug Discov. Mar. 2016;15(3):173-83. doi: 10.1038/nrd.2015.10. Epub Jan. 29, 2016. Review.

Maltsev et al., Stable Peptides Instead of Stapled Peptides: Highly Potent $\alpha v\beta 6$-Selective Integrin Ligands. Angew Chem Int Ed Engl. Jan. 22, 2016;55(4):1535-9. doi: 10.1002/anie.201508709. Epub Dec. 9, 2015.

Marelli et al., Tumor Targeting via Integrin Ligands. Front Oncol. Aug. 30, 2013;3:222. doi: 10.3389/fonc.2013.00222. Review.

Martin et al., Solid-phase-assisted synthesis of targeting peptide-PEG-oligo(ethane amino)amides for receptor-mediated gene delivery. Org Biomol Chem. Apr. 28, 2012;10(16):3258-68. doi: 10.1039/c2ob06907e. Epub Mar. 12, 2012.

Mas-Moruno et al., $\alpha v\beta 3$- or $\alpha 5\beta 1$-Integrin-Selective Peptidomimetics for Surface Coating. Angew Chem Int Ed Engl. Jun. 13, 2016;55(25):7048-67. doi: 10.1002/anie.201509782. Epub Jun. 3, 2016. Review.

Pameijer et al., Conversion of a tumor-binding peptide identified by phage display to a functional chimeric T cell antigen receptor. Cancer Gene Ther. Jan. 2007;14(1):91-7. Epub Oct. 6, 2006.

Schottelius et al., Ligands for mapping alphavbeta3-integrin expression in vivo. Acc Chem Res. Jul. 21, 2009;42(7):969-80. doi: 10.1021/ar800243b.

Wagstaff et al., NMR relaxation and structural elucidation of peptides in the presence and absence of trifluoroethanol illuminates the critical molecular nature of integrin $\alpha v\beta 6$ ligand specificity. RSC Adv. Nov. 21, 2012;2(29):11019-11028. Epub Sep. 17, 2012.

Zhu et al., 99mTc-labeled cystine knot peptide targeting integrin $\alpha v\beta 6$ for tumor SPECT imaging. Mol Pharm. Apr. 7, 2014;11(4):1208-17. doi: 10.1021/mp400683q. Epub Feb. 24, 2014.

\* cited by examiner

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 1

LIGANDS FOR INTEGRIN αVβ8, SYNTHESIS AND USES THEREOF

CROSS REFERENCE TO RELATED APPLICATION(S)

This Application is a National Stage filing under 35 U.S.C. 371 of International Patent Application No. PCT/EP2018/056733, filed Mar. 16, 2018, which claims priority to European Application Number 17161590.9, filed Mar. 17, 2017. The entire contents of these applications are incorporated herein by reference in their entirety.

1. TECHNICAL FIELD

The present invention pertains to the field of peptide-based pharmaceuticals. In particular, the present invention provides peptides and modified peptides, which bind to αvβ8 integrin with high activity and selectivity. Due to these binding properties, the inventive compounds are useful in a variety of applications including use as therapeutic agent, diagnostic agent, targeting moiety and biomolecular research tool.

2. BACKGROUND OF THE INVENTION

The family of human heterodimeric integrin receptors consists of 24 members, which differ from each other in α and β subunits. Eight integrins of this superfamily (αvβ1, αvβ3, αvβ5, αvβ6, αvβ8, α5β1, α8β1 and αIIbβ3) are able to recognize the RGD tripeptide fragment in natural and artificial ligands with varying activity and selectivity [T. G. Kapp, F. Rechenmacher, S. Neubauer, O. V. Maltsev, A. E. Cavalcanti-Adam, R. Zarka, U. Reuning, J. Notni, H.-J. Wester, C. Mas-Moruno, J. P. Spatz, B. Geiger, H. Kessler; A Comprehensive Evaluation of the Activity and Selectivity Profile of Ligands for RGD-binding Integrins, Scientific Reports 2017 7:39805|DOI: 10.1038/srep39805]. The role of individual integrin subtypes and their cross-talks are only partially investigated due to lack of active and highly selective ligands, which are able to interact with only one single integrin subtype.

Nevertheless, already now the significance of distinct integrin subtypes in different diseases is established. That makes integrins of great interest from medical point of view [T. G. Kapp, F. Rechenmacher, T. R. Sobahi, H. Kessler, Integrin modulators: a patent review, *Exp. Opin. Patent Reviews* 2013, 23, 1273-1295. Desgrosellier, J. S. & Cheresh, D. A. Integrins in cancer: biological implications and therapeutic opportunities *Nat. Rev. Cancer* 2010, 10, 9-22. doi: 10.1038/nrc2748. Ley, K.; Rivera-Nieves, J.; Sandbom, W. J. & Shattil, S. Integrin-based Therapeutics: Biological Basis, Clinical Use and New Drugs, *Nat. Rev. Drug Disc.* 2016, 15, 173-183. doi:10.1038/nrd.2015.10. Goodman, S. L. & Picard, M. Integrins as therapeutic targets *Trends Pharmacol. Sci.* 2012, 33, 405-412. doi: 10.1016/j.tips.2012.04.002].

For example, integrin αvβ8 is used by the Foot-and-Mouth-Disease virus (FMDV) and other viruses to enter host cells [J. Du, H. Chang et al. Mol Cell Probes 2010 24, 258-65: doi: 10.1016/j.mcp.2010.04.005] and is highly up-regulated in the course of multiple types of cancer and fibrosis [J. J. Worthington; A. Kelly; C. Smedley, et al. Immunity 2015, 42, 903-915]. For instance, the integrin αvβ8 is up-regulated in nearly 90% of all squamous cell carcinomas, pancreatic tumors and tumors of the ovaries [Y. Hayashido, H. Kitano et al. Int. J. Oncol. 2014, 45, 1875-82, doi: 10.3892/ijo.2014.2642;]. Up-regulation is also found in other cancer types, such as, for instance, in 40% of all types of lung cancers, colon cancers and breast cancers. The involvement of αvβ8 in angiogenesis is proven in several studies [S. Hirota, Q. Kiu, H. S. Lee, M. G. Hossain, A. Lacy-Hulbert, J. H. McCarthy, Development 2011, 138, 5157-66: 10.1242/dev.069153; S. Cambier et al. Am. J. Pathol, 2005, 166, 1883-94]. This integrin, similar to integrin αvβ6 activates tumor growth factor beta (TGF-β) [Dong, X. et al. Nature http://dx.doi.org/10.1038/nature21035 (2016). H. Ha Nature 2017, 1-2: doi: 10.1038/nature21119] and the individual differences between the two integrins are largely unexplored.

Antibodies binding specifically to the αvβ8 integrin are known. However, the development and manufacture of such antibodies is complex, time consuming and costly. Moreover, antibodies suffer from the problem that they have a higher risk of causing undesired side effects of the human immune system. Moreover, antibodies are sometimes problematic when used for imaging purposes (e.g. due to undesired binding to serum albumin).

So far no small molecule ligand is known that is highly active for αvβ8 integrin and at the same time possesses no binding affinity toward other RGD-recognizing integrins (Kapp et al Sci. Rep. 2017 as cited above). The expression of integrins αvβ6 and αvβ8 differs between subjects suffering from different medical conditions. It can even differ between individual subjects suffering from the same medical condition. Therefore, while multi-selective ligands for members of the RGD-recognizing integrin subfamily might also have medicinal use (C. Mas-Moruno, F. Rechenmacher, H. Kessler, Anti-cancer agents in medicinal chemistry 2010, 10, 753-768), a small molecule compound permitting selective targeting of the αvβ8 integrin would be particularly valuable for therapeutic uses, including personalized medicine, especially after diagnostic identification of the integrin subtype via imaging methods with the here described ligand. The ligands of integrin αvβ8 are valuable research tools as well.

3. SUMMARY OF THE INVENTION

Having regard to the above situation, there is a need for novel small molecule functionalized or non-functionalized αvβ8-ligands that can be used as drugs or as tools for molecular imaging and diagnosis (PET/SPECT/UV-Vis tracers), for coating of medicinal relevant surfaces or for biophysical investigations of the function of this integrin subtype.

As our recently developed ligand for αvβ6 had some residual activity for αvβ8 we used this as starting point for the development of a highly active and selective αvβ8 integrin ligand. Surprisingly, significant improvements in affinity and selectivity could be accomplished by reducing the number of residues from a nonapeptide to an octapeptide. Subnanomolar binding affinity for αvβ8 and a two orders of magnitude lower affinity for αvβ6 can be accomplished with an appropriate amino acid sequence of the octapeptide. No binding to other RGD recognizing integrins is found for such peptides of the present invention. It was thus surprisingly found that low molecular weight 8-mer cyclic peptides of general formula (I) possess sub-nanomolar activity for αvβ8 integrin and show high selectivity against other RGD-binding integrins.

One structural feature of the compounds of the invention is the presence of a dipeptide sequence, which may be D-Pro-L-Pro or a related sequence, which induces an optimal conformation of the amino acids responsible for binding to the αvβ8 receptor. In this respect, the compounds of the present invention are similar to the above-mentioned nonapeptide ligand for the αvβ6 integrin.

The compounds of the present invention are thus characterized by the general formula (I)

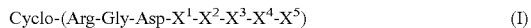

Cyclo-(Arg-Gly-Asp-$X^1$-$X^2$-$X^3$-$X^4$-$X^5$)   (I)

The variable groups in general formula (I) have the meanings specified in appended claim 1. Preferred embodiments of the compounds of the present invention are characterized in appended dependent claims 2 to 6.

The highly active and selective binding to αvβ8 integrin allows using the compounds of the present invention as a drug for the treatment of medical indications wherein expression of αvβ8 integrin is up-regulated and/or wherein αvβ8 integrin is involved in the molecular mechanism of the indication. Such therapeutic uses of the compounds of the present invention are specified in appended claims 8 to 10.

The substitution of L-proline by N-methyl-L-lysine in position $X^3$ is possible and allows to functionalize ligands for instance with fluorescent dyes or other labeling groups with only small loss of activity (less than one order of magnitude) or selectivity (e.g. binding affinity for the integrin αvβ6 that is two orders of magnitude smaller). The fluorescent labeled ligands can be applied for diagnostic applications. Such applications are specified in appended claim 11.

The present invention also provides pharmaceutical compositions as specified in appended claims 7 and 12. Finally, it provides methods for the synthesis of the compounds of the present invention. Such methods are specified in appended claims 13 and 14.

4. DETAILED DESCRIPTION

4.1. Definitions

Unless specified otherwise, standard amino acid nomenclature is used. Unless specified otherwise, amino acids are L-stereoisomers. Unless specified otherwise, amino acid moieties are linked to each other via peptide bonds.

Sar refers to Sarcosine.

Nle refers to Norleucine.

Me refers to a methyl group.

N-Me-amino acid refers to a group, wherein the α-amino group carries a methyl group; For instance, N-Me-Lys refers to N-methyl-lysine and N-Me-Gln refers to N-methyl-glutamine. Similarly, N-Me-D-Phe refers to the D-enantiomer of N-methyl-phenylalanine. Lys(Ac) refers to a lysine residue, wherein the ω-amino group carries an acetyl group.

Unless the context dictates otherwise, references to the "compound of the invention" are to be understood as references not only to the compound of the present invention according to general formula (I) described herein below, but also as references to the pharmaceutically acceptable salts, esters, solvates, polymorphs or modified forms thereof as represented by the general formula (II) described herein below.

The term "amino acid" generally refers to an organic compound comprising both a carboxylic acid group and an amine group. Unless specified otherwise, the term "amino acid" is intended to cover both natural and synthetic amino acids, but wherein the use of natural amino acids is preferred. The term "natural amino acid" and equivalent expressions refer to amino acids commonly found in naturally occurring proteins. Examples of natural amino acids include, without limitation, alanine (Ala), cystein (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asp), proline (Pro), glutamine (Gln), arginine (Arg), serine (Ser), threonine (Thr), valine (Val), tryptophan (Trp), and tyrosine (Tyr).

It will be understood that "carries", "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. Unless specified otherwise, the term "substituted", when in association with any of the below groups refers to a group substituted at one or more position with substituents such as alkyl, alkenyl, alkynyl, alkoxy, acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, cycloalkyl, heterocycloalkyl, aryl, heteroaryl, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g. if the group contains an alkyl group, an aryl group, or other.

Unless specified otherwise, all abbreviations are intended to have their commonly used meaning as represented, for instance, by the IUPAC-IUP Commission on Biochemical Nomenclature in Biochemistry 11, 1972, 942-944.

Unless specified otherwise, compounds of the present invention are "pharmaceutically acceptable" which means that the respective compounds are suitable for use with humans and/or animals without causing adverse effects (such as irritation or toxicity), commensurate with a reasonable benefit/risk ratio.

The term "or" is generally employed in its sense including "and/or" unless the content clearly dictates otherwise.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

The symbol "-" in general represents a bond between two atoms in the chain. In addition, the symbol "-" also represents the point of attachment of the substituent to a compound. Thus for example aryl($C_1$-$C_6$)alkyl- indicates an arylalkyl group, such as benzyl, attached to the compound through the alkyl moiety.

Where multiple substituents are indicated as being attached to a structure, it is to be understood that the substituent can be the same or different.

As used herein, the term "alkyl" refers to saturated hydrocarbons having from one to sixteen carbon atoms, more preferably from one to six carbon atoms, including linear or branched alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, and the like. The term "$C_1$-$C_n$alkyl" refers to an alkyl group having from 1 to the indicated "n" number of carbon atoms. The term "alkylene" group refers to a group derived from an alkyl group as defined above, but having two valencies instead of the single valency of the alkyl group. Preferably, the two free valencies are at opposing termini of the alkylene group.

As used herein, the term "alkenyl" refers to unsaturated hydrocarbons having from two to sixteen carbon atoms, more preferably from two to six carbon atoms, including linear or branched alkenyl groups, and comprising between one and six carbon-carbon double bonds. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, and the like. The term alkenyl includes both unsubstituted alkenyl groups and substituted alkenyl groups. The term "$C_2$-$C_n$alkenyl" refers to an alkenyl group having from 2 to the indicated "n" number of carbon atoms. The term "alkenylene" group refers to a group derived from an alkenyl group as defined above, but having two valencies instead of the single valency of the alkenyl group. Preferably, the two free valencies are at opposing termini of the alkenylene group.

As used herein, the term "alkynyl" refers to unsaturated hydrocarbons having from two to twelve carbon atoms, more preferably from two to six carbon atoms, including linear or branched alkynyl groups, and comprising between one to six carbon-carbon triple bond. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "$C_2$-$C_n$alkynyl" refers to an alkynyl group having from 2 to the indicated "n" number of carbon atoms. The term "alkynylene" group refers to a group derived from an alkynyl group as defined above, but having two valencies instead of the single valency of the alkynyl group. Preferably, the two free valencies are at opposing termini of the alkynylene group.

The terms "cycloalkyl", "carbocyclic" and equivalent expressions refer to a group comprising a saturated or partially unsaturated (non aromatic) carbocyclic ring in a monocyclic or polycyclic ring system, including spiro (sharing one atom) or fused (sharing at least one bond) carbocyclic ring systems, having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl" refers to a cycloalkyl group having from 3 to the indicated "n" number of carbon atoms in the ring structure.

The term "heterocycloalkyl" and equivalent expressions refer to a group comprising a saturated or partially unsaturated (non aromatic) carbocyclic ring in a monocyclic or polycyclic ring system, including spiro (sharing one atom) or fused (sharing at least one bond) carbocyclic ring systems, having from three to fifteen ring members, where one or more (up to six) ring members are substituted or unsubstituted heteroatoms (e.g. N, O, S, P) or groups containing such heteroatoms (e.g. NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g. via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, quinolizinyl, and sugars, and the like.

The term heterocycloalkyl includes both unsubstituted heterocycloalkyl groups and substituted heterocycloalkyl groups. The term "$C_3$-$C_n$heterocycloalkyl" refers to a heterocycloalkyl group having from 3 to the indicated "n" number of atoms (carbon or heteroatom or group) in the ring structure, including at least one hetero group or atom as defined above.

The terms "aryl" and "aryl ring" refer to aromatic groups having 4n+2 π(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl" refers to an aryl group having from 6 to the indicated "n" number of carbons in the ring structure.

The terms "heteroaryl" and "heteroaryl ring" refer to aromatic groups having 4n+2 π(pi) electrons, wherein n is an integer from 1 to 3, in a conjugated monocyclic or polycyclic system (fused or not) and having five to fourteen ring members, including one to six substituted or unsubstituted heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g. via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, 3H-indolyl, indolinyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl" refers to an heteroaryl group having from 5 to the indicated "n" number of atoms (carbon or heteroatom or group) in the ring structure, including at least one hetero group or atom as defined above.

The terms "heterocycle" or "heterocyclic" or "heterocyclyl" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —NR$^a$R$^b$, in which R$^a$ and R$^b$ are each independently hydrogen, alkyl, aryl, or heterocyclyl, or R$^a$ and R$^b$, taken together with the nitrogen atom to which they are attached, form a heterocyclic ring. The term "amide" or "aminocarbonyl" includes compounds or moieties which contain a nitrogen atom which is bound to the carbon of a carbonyl or a thiocarbonyl group. The term acylamino refers to an amino group directly attached to an acyl group as defined herein.

The term "nitro" means —NO$_2$; the term "halogen" refers to bromine, chlorine, fluorine or iodine substituents; the term "thiol" means SH; and the term "hydroxyl" or "hydroxy" means —OH. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The term "alkoxy" as used herein means an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like. The term alkoxy includes both unsubstituted or substituted alkoxy groups, etc., as well as halogenated alkyloxy groups.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group ($C_1$-$C_n$alkyl, $C_1$-$C_n$alkenyl, $C_1$-$C_n$alkynyl, wherein n is an integer from 2 to 10; e.g. acetyl, a cycloalkyl group (e.g. $C_3$-$C_8$cycloalkyl), a heterocyclic group (e.g. $C_3$-$C_8$heterocycloalkyl and $C_5$-$C_6$heteroaryl), an aromatic group (e.g. $C_6$aryl, e.g., benzoyl), and the like. Acyl groups may be unsubstituted or substituted acyl groups (e.g. salicyloyl).

The term "solvate" refers to a physical association of a compound of this invention with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, hemiethanolates, and the like, preferably hydrates.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that takes advantage of an intrinsically basic, acidic or charged functionality on the molecule and that is not biologically or otherwise undesirable. Example of pharmaceutically acceptable salts are also described, for example, in Berge et al., "Pharmaceutical Salts", *J. Pharm. Sci.* 66, 1-19 (1977). Such salts include: (1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, 3-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like; (2) base addition salts, formed when an acidic proton present in the parent compound either is replaced by a metal ion, including, an alkali metal ion (e.g. lithium, sodium, potassium), an alkaline earth ion (e.g. magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from the parent compound that contains a basic or acidic moiety, by conventional chemical methods. Generally, such salts are prepared by reacting the free acid or base forms of these compounds with a stoichiometric amount of the appropriate base or acid in water or in an organic solvent, or in a mixture of the two. Salts may be prepared in situ, during the final isolation or purification of the agent or by separately reacting a purified compound of the invention in its free acid or base form with the desired corresponding base or acid, and isolating the salt thus formed. The term "pharmaceutically acceptable salts" also include zwitterionic compounds containing a cationic group covalently bonded to an anionic group, as they are "internal salts".

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

"Pharmaceutically acceptable vehicle" or "pharmaceutically acceptable carrier" refers to a diluent, adjuvant, excipient, or carrier with which a compound is administered.

"Pharmaceutical composition" refers to at least one compound and at least one pharmaceutically acceptable vehicle or carrier, with which the compound is administered to a patient.

4.2. Compounds of the Invention

The compounds of the present invention are characterized by the following general formula (I):

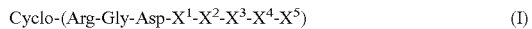

Cyclo-(Arg-Gly-Asp-$X^1$-$X^2$-$X^3$-$X^4$-$X^5$)      (I)

wherein the variables groups $X^1$ to $X^5$ have the following meanings $X^1$: Leu, Ile, Nle, Val, Tyr, Phe $X^2$: D-amino acid such as D-Pro, N-Me-D-Phe $X^3$: Pro, Pro-$R^{x3}$, N-Me-amino acid such as N-Me-Lys, N-Me-Lys(Ac), N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$ $X^4$: Gly, Ala, Ser, Thr $X^5$: Leu, Ala, Tyr, His, Ile, Nle, Val, Phe The above residue Pro-$R^{x3}$ represents a proline residue that is functionalized at the C-3, C-4 or C-5 carbon atom and preferably the C-4 carbon atom with a functional group selected from —$NH_2$, —OH, —NH—Ac, —NH-L4-R4, wherein L4 is selected from the group consisting of covalent bond, —C(O)—, and —C(O)—O—, and wherein R4 is selected from the group consisting of —$(CH_2)_n$—C≡CH and —$(CH_2)_n$—$N_3$ with n=0, 1, 2, 3, 4, 5, 6, 7, 8, 9 or 10, such as —NH-butyne, —NH-pentyne, —NH-hexyne, —NH-heptyne. Pro-$R^{x3}$ may further represent aza-proline residues carrying one of the above functional groups listed in this paragraph.

The above residue Lys-$R^{x4}$ represents a residue derived from a lysine residue, wherein the ω-amino nitrogen atom carries a group of the formula -L4-R4, wherein L4 is selected from the group consisting of covalent bond, —C(O)—, and —C(O)—O—, . . . , and wherein R4 is selected from the group consisting of —$(CH_2)_n$—C≡CH and —$(CH_2)_n$—$N_3$ with n=0, 1, 2, 3, 4, 5, 6, 7, 8, 9 or 10.

The above residue N-Me-Lyy represents a residue related to N-methyl-lysine but having a modified length of the side chain. N-Me-Lyy represents in particular the residues covered by the following general formula: —$N(CH_3)$—CH($R^{Lyy}$)—CO—, wherein $R^{Lyy}$ represents —$(CH_2)_y$—$NH_2$ with y=1, 2, 3, 5, 6, 7, 8, 9 or 10.

The above residue N-Me-Lyy-$R^{x4}$ represents a residue derived from N-Me-Lyy, wherein the side chain amino nitrogen atom carries a group of the formula -L4-R4, wherein L4 is selected from the group consisting of covalent bond, —C(O)—, and —C(O)—O—, and wherein R4 is selected from the group consisting of —$(CH_2)_n$—C≡CH and —$(CH_2)_n$—$N_3$ with n=0, 1, 2, 3, 4, 5, 6, 7, 8, 9 or 10.

The above residue N-Me-Gln-$R^{x4}$ is a residue derived from N-Me-Gln, wherein the nitrogen atom of the side chain carries a group of the formula -L4-R4, wherein L4 is selected from the group consisting of covalent bond, —C(O)—, and —C(O)—O—, and wherein R4 is selected from the group consisting of —$(CH_2)_n$—C≡CH and —$(CH_2)_n$—$N_3$ with n=0, 1, 2, 3, 4, 5, 6, 7, 8, 9 or 10.

The above residue N-Me-Gyy represents a residue related to N-Me-Gln but having a modified length of the side chain. N-Me-Gyy represents in particular the residues covered by the following general formula: —$N(CH_3)$—CH($R^{Gyy}$)—CO—, wherein $R^{Gl}$ represents —$(CH_2)_y$—CO—$NH_2$ with y=1, 3, 5, 6, 7, 8, 9 or 10.

The above residue N-Me-Gyy-$R^{x4}$ represents a residue derived from N-Me-Gyy, wherein the nitrogen atom of the side chain carries a group of the formula -L4-R4, wherein L4 is selected from the group consisting of covalent bond, —C(O)—, and —C(O)—O—, and wherein R4 is selected from the group consisting of —$(CH_2)_n$—C≡CH and —$(CH_2)_n$—$N_3$ with n=0, 1, 2, 3, 4, 5, 6, 7, 8, 9 or 10.

The sub-sequence -$X^2$-$X^3$- may also represent a β-turn mimetic differing from the meanings above, such as disclosed, for instance, in U. Nagai, K. Sato, Tetr. Lett. 1985, 26, 647; Feigel et. al. JACS 1986, 108, 181; H. Diaz, J. W. Kelly, Tetr. Lett. 1991, 32, 5725; Feigel et. al. Helv. Chem. Acta 1994, 77, 70; J. A. Robinson et. al. Angew. Chem. 2004, 116, 2161; and Kessler et. al. J. Am. Chem. Soc. 1996, 118, 7881.

The compounds of the present invention may also be in the form of a pharmaceutically acceptable salts, esters, solvates, polymorphs or modified forms thereof. Pharmaceutically acceptable salt may include, for instance, salts formed by reaction of acidic residues with inorganic or organic alkaline substances as well as salts formed by reaction of basic residues with inorganic or organic acids. Preferred salts are sulfates, nitrates, chlorides, bromides, phosphates, sulfonates, tartrates, formates, maleates, malates, citrates, benzoates, ascorbates, etc. Pharmaceutically acceptable esters may be esters formed by reaction of side chain hydroxyl groups in Tyr residues with suitable carboxylic acids typically having from 2 to 20 carbon atoms. Solvates may be formed by crystallizing the compounds of the invention with any pharmaceutically acceptable solvent including, for instance, water and ethanol. As regards polymorphs, there is no particular limitation. The amorphous form can also be used. Modified forms of the compound of the present invention include the specific modified compounds described below by reference to general formula (II). Further modified forms of the compound of the present invention may include compounds of the present invention that have been modified by covalently attaching pharmaceutically acceptable moieties such as $C_{1-20}$ alkyl groups via hydrolyzable groups to generate a prodrug form of the compounds of the present invention. Such suitable modifications are described, for instance, on page 11 in lines 10 to 25 of WO 01/05810.

Preferred compounds of the present invention are characterized by the above general formula (I), wherein the variable groups $X^1$ to $X^5$ have the following more specific meanings.

Embodiment 1

$X^1$: Leu
$X^2$: D-amino acid such as D-Pro, N-Me-D-Phe
$X^3$: Pro, N-Me-amino acid such as N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala, Ser, Thr
$X^5$: Leu, Tyr, His, Ala, Ile, Nle, Val, Phe Embodiment 2

$X^1$: Leu, Ile, Nle, Val, Tyr, Phe
$X^2$: D-Pro, N-Me-D-Phe
$X^3$: Pro, N-Me-amino acid such as N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala, Ser, Thr
$X^5$: Leu, Tyr, His, Ala, Ile, Nle, Val, Phe Embodiment 3

$X^1$: Leu, Ile, Nle, Val, Tyr, Phe
$X^2$: D-amino acid such as D-Pro, N-Me-D-Phe
$X^3$: Pro, N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala, Ser, Thr
$X^5$: Leu, Tyr, His, Ala, Ile, Nle, Val, Phe Embodiment 4

$X^1$: Leu, Ile, Nle, Val, Tyr, Phe
$X^2$: D-amino acid such as D-Pro, N-Me-D-Phe
$X^3$: Pro, N-Me-amino acid such as N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala
$X^5$: Leu, Tyr, His, Ala, Ile, Nle, Val, Phe Embodiment 5

$X^1$: Leu, Ile, Nle, Val, Tyr, Phe
$X^2$: D-amino acid such as D-Pro, N-Me-D-Phe
$X^3$: Pro, N-Me-amino acid such as N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala, Ser, Thr
$X^5$: Leu, Tyr, His, Ala, Phe Embodiment 1.1

$X^1$: Leu
$X^2$: D-Pro
$X^3$: Pro, N-Me-amino acid such as N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala, Ser, Thr
$X^5$: Leu, Tyr, His, Ala, Ile, Nle, Val, Phe Embodiment 1.2

$X^1$: Leu
$X^2$: D-Pro
$X^3$: Pro, N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala, Ser, Thr
$X^5$: Leu, Tyr, His, Ala, Ile, Nle, Val, Phe

Embodiment 1.3

$X^1$: Leu
$X^2$: D-Pro
$X^3$: Pro, N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala
$X^5$: Leu, Tyr, His, Ala, Ile, Nle, Val, Phe

Embodiment 1.4

$X^1$: Leu
$X^2$: D-Pro
$X^3$: Pro, N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly, Ala
$X^5$: Leu, Tyr, His, Ala, Phe

Embodiment 1.5

$X^1$: Leu
$X^2$: D-Pro
$X^3$: Pro, N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly,
$X^5$: Leu, Tyr, His, Ala, Phe

Embodiment 1.6

$X^1$: Leu
$X^2$: D-Pro
$X^3$: Pro, N-Me-Lys, N-Me-Lys(Ac); Pro-$R^{x3}$, N-Me-Lys-$R^{x4}$, N-Me-Lyy, N-Me-Lyy-$R^{x4}$, N-Me-Gln, N-Me-Gln-$R^{x4}$, N-Me-Gyy, N-Me-Gyy-$R^{x4}$
$X^4$: Gly,
$X^5$: Leu, Tyr, His

Embodiment 1.7

$X^1$: Leu
$X^2$: D-Pro
$X^3$: Pro, Pro-$R^{x3}$, N-Me-Lys-$R^{x4}$, N-Me-Lyy-$R^{x4}$, N-Me-Gln-$R^{x4}$, N-Me-Gyy-$R^{x4}$
$X^4$: Gly,
$X^5$: Leu, Tyr, His

Embodiment 1.8

$X^1$: Leu
$X^2$: D-Pro, N-Me-D-Phe

X³: Pro, N-Me-amino acid such as N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}

X⁴: Gly, Ala, Ser, Thr

X⁵: Leu, Tyr, His, Ala, Phe

Embodiment 1.9

X¹: Leu
X²: D-Pro, N-Me-D-Phe
X³: Pro, N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}
X⁴: Gly, Ala, Ser, Thr
X⁵: Leu, Tyr, His, Ala, Phe

Embodiment 1.10

X¹: Leu
X²: D-Pro, N-Me-D-Phe
X³: Pro, N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}
X⁴: Gly, Ala
X⁵: Leu, Tyr, His, Ala, Phe

Embodiment 1.11

X¹: Leu
X²: D-Pro, N-Me-D-Phe
X³: Pro, N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}
X⁴: Gly, Ala
X⁵: Leu, Tyr, His

Embodiment 1.12

X¹: Leu
X²: D-Pro
X³: Pro, N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}
X⁴: Gly, Ala
X⁵: Leu, Tyr, His

Embodiment 1.13

X¹: Leu
X²: D-Pro
X³: Pro, N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}
X⁴: Gly
X⁵: Leu, Tyr, His

Embodiment 1.14

X¹: Leu
X²: D-Pro
X³: Pro, N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}
X⁴: Gly
X⁵: Leu

Embodiment 1.15

X¹: Leu
X²: D-Pro
X³: Pro
X⁴: Gly, Ala
X⁵: Leu, Tyr, His

Embodiment 1.16

X¹: Leu
X²: D-Pro
X³: Pro
X⁴: Gly
X⁵: Leu, Tyr, His

Embodiment 1.17

X¹: Leu
X²: D-Pro
X³: Pro
X⁴: Gly, Ala
X⁵: Leu

Embodiment 1.18

X¹: Leu
X²: D-Pro
X³: Pro, Pro-R^{x3}
X⁴: Gly, Ala
X⁵: Leu, Tyr, His

Embodiment 2.1

X¹: Leu, Ile, Nle, Val, Tyr, Phe
X²: D-Pro, N-Me-D-Phe
X³: Pro, N-Me-amino acid such as N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}
X⁴: Gly, Ala, Ser, Thr
X⁵: Leu, Ala, Tyr, His, Ile, Nle, Val, Phe Embodiment 2.2

X¹: Leu, Ile, Nle, Val, Tyr, Phe
X²: D-Pro, N-Me-D-Phe
X³: Pro, N-Me-Lys, N-Me-Lys(Ac); Pro-R^{x3}, N-Me-Lys-R^{x4}, N-Me-Lyy, N-Me-Lyy-R^{x4}, N-Me-Gln, N-Me-Gln-R^{x4}, N-Me-Gyy, N-Me-Gyy-R^{x4}
X⁴: Gly, Ala, Ser, Thr
X⁵: Leu, Ala, Tyr, His, Ile, Nle, Val, Phe

Embodiment 2.3

X¹: Leu, Ile, Nle, Val, Tyr, Phe
X²: D-Pro, N-Me-D-Phe

X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser
X⁵: Leu, Ala, Tyr, His, Ile, Nle, Val, Phe

Embodiment 2.4

X¹: Leu, Ile, Nle, Val, Tyr, Phe
X²: D-Pro, N-Me-D-Phe
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser
X⁵: Leu, Ala, Tyr, His, Phe

Embodiment 2.5

X¹: Leu, Ile, Nle, Val, Tyr, Phe
X²: D-Pro
X³: Pro, N-Me-amino acid such as N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser, Thr
X⁵: Leu, Ala, Tyr, His, Ile, Nle, Val, Phe Embodiment 2.6

X¹: Leu, Ile, Nle, Val, Tyr, Phe
X²: D-Pro
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser, Thr
X⁵: Leu, Ala, Tyr, His, Ile, Nle, Val, Phe

Embodiment 2.7

X¹: Leu, Ile, Nle, Val, Tyr, Phe
X²: D-Pro
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser
X⁵: Leu, Ala, Tyr, His, Ile, Nle, Val, Phe

Embodiment 2.8

X¹: Leu, Ile, Nle, Val, Tyr, Phe
X²: D-Pro
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser
X⁵: Leu, Ala, Tyr, His, Phe

Embodiment 3.1

X¹: Leu, Ile, Nle, Val, Tyr, Phe
X²: D-amino acid such as D-Pro, N-Me-D-Phe
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser, Thr
X⁵: Leu, Ala, Tyr, His, Ile, Nle, Val, Phe Embodiment 3.2

X¹: Leu, Ile, Nle, Val, Tyr, Phe
X²: D-amino acid such as D-Pro, N-Me-D-Phe
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser
X⁵: Leu, Ala, Tyr, His, Ile, Nle, Val, Phe Embodiment 3.3

X¹: Leu, Ile, Nle, Val, Tyr, Phe
X²: D-amino acid such as D-Pro, N-Me-D-Phe
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser
X⁵: Leu, Ala, Tyr, His, Phe Embodiment 3.4

X¹: Leu
X²: D-amino acid such as D-Pro, N-Me-D-Phe
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser
X⁵: Leu, Ala, Tyr, His, Phe Embodiment 3.5

X¹: Leu, Ile, Nle, Val
X²: D-Pro, N-Me-D-Phe
X³: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser
X⁵: Leu, Ala, Tyr, His, Phe

Embodiment 3.6

X¹: Leu, Ile, Nle, Val, Tyr, Phe
X²: D-amino acid such as D-Pro, N-Me-D-Phe
X³: Pro, Pro-R$^{x3}$, N-Me-Lys-R$^{x4}$, N-Me-Lyy-R$^{x4}$, N-Me-Gln-R$^{x4}$, N-Me-Gyy-R$^{x4}$
X⁴: Gly, Ala, Ser, Thr
X⁵: Leu, Ala, Tyr, His, Ile, Nle, Val, Phe Embodiment 3.7

X¹: Leu, Ile, Nle, Val, Tyr, Phe
X²: D-amino acid such as D-Pro, N-Me-D-Phe
X³: Pro, Pro-R$^{x3}$, N-Me-Lys-R$^{x4}$, N-Me-Lyy-R$^{x4}$, N-Me-Gln-R$^{x4}$, N-Me-Gyy-R$^{x4}$
X⁴: Gly, Ala
X⁵: Leu, Ala, Tyr, His, Phe Embodiment 4.1

X¹: Leu, Ile, Nle, Val, Tyr, Phe
X²: D-amino acid such as D-Pro, N-Me-D-Phe
X³: Pro, N-Me-amino acid such as N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$ X⁴: Gly, Ala,
X⁵: Leu, Ala, Tyr, His, Ile, Nle, Val, Phe Embodiment 4.2

X¹: Leu, Ile, Nle, Val, Tyr, Phe
X²: D-amino acid such as D-Pro, N-Me-D-Phe
X³: Pro, N-Me-amino acid such as N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala,
X⁵: Leu, Ala, Tyr, His, Phe Embodiment 4.3

X¹: Leu, Ile, Nle, Val, Tyr, Phe
X²: D-amino acid such as D-Pro, N-Me-D-Phe
X³: Pro, N-Me-amino acid such as N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly
X⁵: Leu, Ala, Tyr, His, Ile, Nle, Val, Phe Embodiment 4.4

X¹: Leu, Ile, Nle, Val, Tyr, Phe
X²: D-amino acid such as D-Pro, N-Me-D-Phe
X³: Pro, N-Me-amino acid such as N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly
X⁵: Leu, Ala, Tyr, His, Phe Embodiment 5.1

X¹: Leu, Ile, Nle, Val, Tyr, Phe
X²: D-amino acid such as D-Pro, N-Me-D-Phe
X³: Pro, N-Me-amino acid such as N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser, Thr
X⁵: Leu, Ala, Tyr, His, Phe Embodiment 5.2

X¹: Leu, Ile, Nle, Val, Tyr, Phe
X²: D-amino acid such as D-Pro, N-Me-D-Phe
X³: Pro, N-Me-amino acid such as N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$
X⁴: Gly, Ala, Ser, Thr
X⁵: Leu, Tyr, His Embodiment 5.3

X¹: Leu
X²: D-Pro
X³: Pro, N-Me-Lys, N-Me-Lys(Ac), N-Me-Lyy, N-Me-Gln, N-Me-Gyy,
X⁴: Gly, Ala
X⁵: Leu, Tyr, His

Embodiment 6.1

X¹: Leu
X²: D-Pro
X³: Pro, Pro-R$^{x3}$, N-Me-Lys-R$^{x4}$, N-Me-Lyy-R$^{x4}$, N-Me-Gln-R$^{x4}$, N-Me-Gyy-R$^{x4}$
X⁴: Gly, Ala
X⁵: Leu, Tyr, His

In further specific embodiments, the present invention pertains to the following specific compounds:
Cyclo-(Arg-Gly-Asp-Leu-D-Pro-Pro-Ala-Leu)
Cyclo-(Arg-Gly-Asp-Leu-D-Pro-Pro-Gly-Leu)
Cyclo-(Arg-Gly-Asp-Leu-D-Pro-Pro-Ser-Leu)
Cyclo-(Arg-Gly-Asp-Leu-D-Pro-Pro-Ala-Tyr)
Cyclo-(Arg-Gly-Asp-Leu-D-Pro-Pro-Ala-His)
Cyclo-(Arg-Gly-Asp-Leu-(N-Me-D-Phe)-Pro-Ala-Leu)
Cyclo-(Arg-Gly-Asp-Leu-D-Pro-Pro-Ala-Leu)
Cyclo-(Arg-Gly-Asp-Leu-D-Pro-(N-Me-Lys)-Gly-Leu)
Cyclo-(Arg-Gly-Asp-Leu-D-Pro-(N-Me-Lys(Ac))-Gly-Leu)
Cyclo-(Arg-Gly-Asp-Leu-D-Pro-Pro-Ala-Ala)
Cyclo-(Arg-Gly-Asp-Leu-D-Pro-(N-Me-Lys-pentyne)-Gly-Leu)
Cyclo-(Arg-Gly-Asp-Leu-D-Pro-(Pro-4-NH-hexyne)-Gly-Leu)
Cyclo-(Arg-Gly-Asp-Leu-D-Pro-Pro-Ala-Phe)
and pharmaceutically acceptable salts, esters, solvates, polymorphs or modified forms thereof.

4.3. Modified Compounds of the Invention

The present invention also pertains to modified compounds. These are compounds of the present invention, as specified above, wherein at least one effector moiety X⁸ is bonded to the peptide via a suitable linker L. The linker may also be multivalent to allow for the bonding of two or more compounds of the present invention and/or two or more effector moieties X⁸. Preferably, the linker according to this embodiment has a total of 3-6 valencies and more preferably 3-5 valencies. The additional one or more valencies of the linker may be used for bonding additional compounds of the invention and/or additional effector moieties.

Specific embodiments of the present invention may thus be characterized by the following general formula (II):

$$(X^0)_{n1}L(X^8)_{n2} \tag{II}$$

wherein X⁰ represents the peptide compound of the invention as specified above (excluding one hydrogen atom to allow bonding to the linker), L represents the linker, X⁸ represents the effector moiety and wherein n1 and n2 are each independently selected from the range of 1 to 5 wherein n1+n2 represents the number of valencies of the linker and is preferably in the range of from 2 to 6, more preferably 3-5 with the proviso that each of n1 and n2 is at least 1. A preferred modified compound of the present invention is the compound, wherein n1=1 and n2=1, i.e. compounds of the following general formula (IIa):

$$X^0\text{-}L\text{-}X^8 \tag{IIa}$$

wherein the meanings of X⁰, L and X⁸ are the same as described above and below.

4.3.1 Position of Modification

In principle, the position of the modification is not particularly restricted, provided that said modification does not significantly affect strength and selectivity of the compound's binding to the αvβ8 integrin. Within the scope of this condition, modified compounds of the invention may be derived from the above specified peptide compounds by replacing any hydrogen atom by -L-$X^8$. This includes all of the compounds of the invention described above, wherein the compounds described above as preferred are also preferred in the context of this modification.

Considering that the stretch of amino acids R-G-D is believed to be most significant for binding to αvβ8 integrin, it is a preferred embodiment of this aspect of the present invention to modify the inventive peptide compound in the position of one of the remaining residues $X^1$, $X^2$, $X^3$, $X^4$, or $X^5$. It is even more preferred to modify one of residues $X^3$, $X^4$, or X. Most preferably, residue $X^3$ is modified.

Within the scope of this most preferred embodiment, it is particularly advantageous to use N-Me-Lys or Pro as residue $X^3$ and to bind the modifying moiety -L-$X^8$ via the ω-amino group of N-Me-Lys or to bind the modifying moiety -L-$X^8$ to the C-4 carbon of Pro. Hence, it is particularly preferred in the context of this embodiment to use the above-mentioned compounds of the present invention, wherein $X^3$ represents N-Me-Lys or Pro. The modified residues Pro-$R^{x3}$ and N-Me-Lys-$R^{x4}$ can be used as building blocks for manufacturing the compound of formula (II) or formula (IIa).

Bonding of the modifying moiety -L-$X^8$ can, for instance, be done by formation of an amide bond by reacting said ω-amino group with an activated carboxyl group forming a terminal group of the linker L. Of course, other functional groups may also be used for attaching the linker to the target amino acid residue and preferably the amino group of residue $X^3$. For instance, the $X^3$ residues Pro-$R^{x3}$, N-Me-Lys-$R^{x4}$, N-Me-Lyy-$R^{x4}$, N-Me-Gln-$R^{x4}$, and N-Me-Gyy-$R^{x4}$ described above are well-suited for bonding the linker via a five-membered heterocycle by means of Click chemistry. The above-mentioned X3 residues Pro, N-Me-Lys, N-Me-Lyy, N-Me-Gln and N-Me-Gyy may furthermore be modified to carry another functional group capable of participating in click chemistry coupling reactions, as described for instance in the Wikipedia article on "Click Chemistry" (Version of Feb. 20, 2017) and in the further literature on click chemistry cited below.

4.3.2 Linker

The linker group L can be any bivalent atomic group wherein the shortest distance between the two valencies is from 3 to 60 covalent bonds, preferably from 5 to 40 covalent bonds, more preferably from 8 to 30 covalent bonds.

The linker may consist of or contain linear, branched and/or cyclic structural elements typically consisting of atoms selected from C, H, N, O, S and P. The total number of heavy atoms (i.e. atoms other than hydrogen) in the linker (including optionally present substituents) may be within the range of 2 and 250, preferably 4 to 100 and more preferably 7 to 60.

In certain embodiments, in particular if a fluorescent dye is used as the effector moiety $X^8$, it may be advantageous to select a linker that is shorter and less rigid than a linker formed by six consecutive proline moieties. Preferred linkers are linkers derived from a single 6-amino hexanoic acid or two consecutive 6-amino hexanoic acids, oligo(ethylene glycol) with three, four or five repeating units, and oligoproline with two, three or four consecutive proline residues. Using such spacers may even improve binding to the target receptor compared to the unmodified cyclopeptide. This is shown experimentally in the appended examples section.

The linker may also carry one or more substituents. Such substituents are preferably selected from the substituents defined above and more preferably from the group consisting of amino, halogen, cyano, nitro, carboxylic acid, carboxylic ester, $C_1$-$C_{20}$ alkyl, $C_2$-$C_{20}$ alkenyl, $C_3$-$C_{20}$ alkynyl, $C_3$-$C_{20}$ cyloalkyl, $C_4$-$C_{20}$ cyloalkenyl, $C_8$-$C_{20}$ cyloalkynyl, $C_6$-$C_{20}$ aryl, $C_1$-$C_6$ alkyl-$C_6$-$C_{20}$ aryl, heteroaryl, 5-7-membered heterocycle having one or more heteroatoms selected from the group consisting of N, O, S and P.

Preferred structural elements contained in the linker are selected from ethylene glycol, polyethylene glycol (PEG) such as PEG with 2-15 ethylene glycol repeating units, propylene glycol, poly propylene glycol (PPG) such as PPG with 2-15 propylene glycol repeating units, amino acids, oligopeptides such as $(Gly)_m$ with m=2-15, saccharides such as galactose and oligosaccharides such as saccharose and other oligosaccharides with 2-15 monosaccharide repeating units. Further structural elements that may be contained in the linker are alkylene groups, alkenylene groups or alkynylene groups, each of them preferably having 2-20 carbon atoms and each of them optionally having incorporated therein one or more carbonyl groups and/or optionally being substituted as explained above. Said structural elements advantageously carry functional groups at their termini to allow bonding to $X^0$, $X^8$ or to other linker structural elements. Said functional groups are preferably derived from hydroxyl groups, amino groups, and carboxyl groups.

Of course, these structural elements can also be combined. Preferred linkers are disclosed in "Ligands for Mapping αvβ3-Integrin Expression in Vivo" by M. Schottelius et al. in *Acc. Chem. Res.* 2009, 42, 969-980, especially the linkers forming part of the structures shown in FIGS. 12 and 14; "Dimerization of a Phage-Display Selected Peptide for Imaging of αvβ6-Integrin: Two Approaches to the Multivalent Effect" by A. N. Singh et al. in *Theranostics* 214, 4, 756-760, especially as shown in Scheme 1. A further linker is shown in "Synthesis and biological evaluation of a peptide-paclitaxel conjugate which targets the integrin αvβ6" by S. Li et al. in *Bioorganic & Medicinal Chemistry* 2011, 19, 5480-5489, and especially the compounds of FIG. 1. Of course, it is also possible to combine two or more different structural elements mentioned above to form a linker.

At its termini, the linker may contain active functional groups to facilitate bonding to the cyclic peptide compound of the invention and bonding to the effector moiety $X^8$. If, for instance, click chemistry is used for coupling the linker to the peptide and/or for coupling the linker to the effector moiety, the functional groups of the linker have to be selected as being complementary to the functional groups of the reaction partner (peptide and/or effector moiety).

According to another preferred embodiment, a linker is used, which contains a hydrolysable group that allows to cleave the two linked moieties. The use of such a cleavable linker may be advantageous, e.g. when the peptide compound $X^0$ is used in order to target a therapeutically active effector moiety $X^8$ (e.g. a cytotoxic agent) to a cell which expresses the αvβ8 integrin (see below). Suitable hydrolysable groups can be selected from ester such as —C(O)—O— and —O—C(O)—, amide (peptide) such as —C(O)—NH— and —NH—C(O)—, carbamate such as —NH—C(O)—O— and —O—C(O)—NH—, urea such as —NH—C(O)—NH— and anhydride such as —C(O)—O—C(O)—. It is of course possible to combine two or more of these hydrolysable groups and/or to combine one or more of these hydrolysable groups with one or more of the optionally substituted linker groups specified above.

4.3.3 Effector Moiety $X^8$

The effector moiety can be a moiety suitable for labelling the compound of the invention, for instance in labelling for imaging purposes such as fluorescence labelling, positron emission tomography (PET), single-photon emission computed tomography (SPECT), optical imaging or magnetic resonance imaging (MRI), X-ray based CT imaging, scintigraphy, ultrasonography and thermography.

Suitable effector moieties for labeling the compounds of the invention are disclosed, for instance, in "Instrumentation and probes for molecular and cellular imaging" by Lecchi et al. in The Quarterly Journal of Nuclear Medicine and Molecular Imaging 2007, 51, 111-26, in "Ligands for Mapping αvβ3-Integrin Expression in Vivo" by M. Schottelius et al. in Acc. Cem. Res. 2009, 42, 969-980, in Scheme 1 of "Dimerization of a Phage-Display Selected Peptide for Imaging of αvβ6-Integrin: Two Approaches to the Multivalent Effect" by A. N. Singh et al. in Theranostics 214, 4, 756-760, in WO 01/05810 especially on page 12, lines 1 to 19 and the reference "The Molecular Probes® Handbook-A Guide to Fluorescent Probes and Labeling Technologies", $11^{th}$ Edition, 2010 by Molecular Probes, Inc./ThermoFisher Scientific.

Effector moieties that can be used as labels for SPECT or PET imaging include various radioisotopes and atomic groups containing one or more of such radioisotopes. If the radioisotope is a metal atom, it is preferred to bind it in the form of a chelate complex. Suitable chelating groups can be selected from 1,10-phenanthroline, ethylene diamine tetraacetic acid, 2,2'-bipyridine, DOTA, NODAGA (see e.g. S. Neubauer et al. *Angew. Chem. Int. Ed.* 2013, 52, 11656-9), or NOPO (J. Šimeček, J. Notni, T. G. Kapp, H. Kessler, H.-J. Wester, *Molecular Pharmaceutics* 2014, 11, 1687-95), TRAP (J. Notni, J. Šimeček, P. Hermann, H.-J. Wester. "TRAP, a Powerful and Versatile Framework for Gallium-68 Radiopharmaceuticals" *Chem. Eur. J.* 2011, 17, 14718-14722.) Suitable chelate complexes of $^{99m}$Tc are disclosed in "$^{99m}$Tc-Labeled Cystine Knot Peptide Targeting Integrin αvβ6 for Tumor SPECT Imaging" by X. Zhu et al. in *Molecular Pharmaceutics* 2014, 11, 1208-1217. Non-metal radioisotopes are preferably bonded in a covalent manner to organic groups. Suitable atomic groups carrying non-metal radioisotopes are disclosed in the Wikipedia entry "List of PET radiotracers" (version of Sep. 16, 2015). A preferred embodiment of the invention relates to a trimerized form of the compound of the invention containing an effector moiety for SPECT or PET imaging, and especially containing the Ga-TRAP effector moiety. Trimerization can increase binding affinity. This is shown by the experimental results provided in the examples section.

Effector moieties that can be used for radio imaging may thus include various radioisotopes and atomic groups (such as chelate complexes) containing the same. Suitable radioisotopes include $^{11}$C, $^{13}$N, $^{15}$O, $^{18}$F, $^{64}$Cu, $^{68}$Ga, $^{88}$Y, $^{89}$Zr, $^{90}$Y, $^{99m}$Tc, $^{111}$In, $^{123}$I, $^{124}$I, $^{131}$I, and $^{177}$Lu. Among these radioisotopes, it is advantageous to use $^{99m}$Tc, 111In, $^{123}$I or $^{131}$I for SPECT imaging and to use $^{11}$C, $^{13}$N, $^{15}$O, $^{18}$F, $^{68}$Ga, $^{82}$Rb or $^{89}$Zr for PET imaging. Materials suitable for use as effector moieties (after bonding to the linker L) are listed in the Wikipedia entries for "Single-photon emission computed tomography", "List of PET radiotracers" (in their versions of Sep. 16, 2015). The Wikipedia entry "Medicinal radiocompounds" (version of Sep. 16, 2015) provides further information on such compounds.

Imaging with the MRI technique can be effected by using a suitable contrast agent as the effector moiety $X^8$. Most preferred are Gd(III) chelate complexes. A description of suitable contrast agents is found, for instance, in the Wikipedia entry "MRI Contrast Agent" (version of Sep. 16, 2015) and documents cited therein. Chelate complexes may be the same as discussed above for the effector moieties for use in SPECT or PET imaging.

Effector moieties that can be used for fluorescence labeling include labels by ThermoFisher commercially available as Cy® series such as CY® 3, 5, 5.5, 7, 7.5 and the AlexaFluor® series such as AlexaFluor® 350, 405, 488, 532, 546, 555, 568, 594, 647, 680, and 750 as well as Fluorescein, Pyren, Rhodamin, BODIPY dyes and their analogues. A further suitable fluorescent dye is the compound commercially available from Li-Cor® under the trade name IRDye® 800CW, which has the following structure (in the form of the reactive NHS-ester, although other forms such as the maleimide form may also be used):

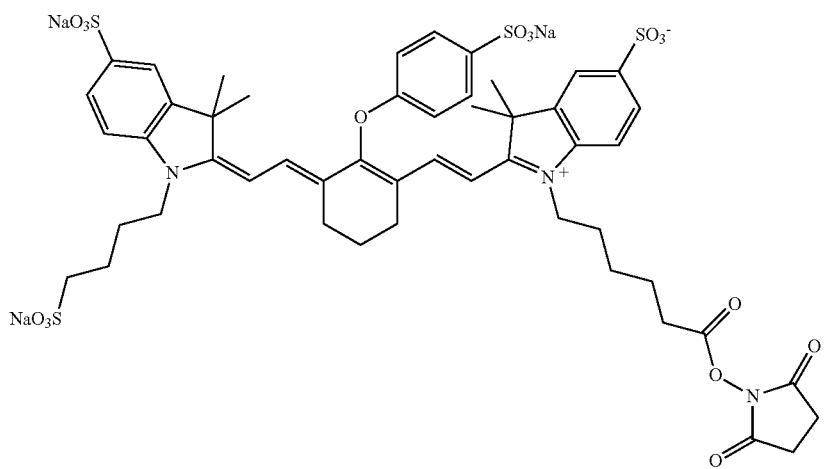

Effector moieties and that can be used for imaging by X-ray-based technology may include, for instance, iodine and atomic groups containing iodine. Materials suitable for use as effector moieties (after bonding to the linker L) are listed in the Wikipedia entry "Radiocontrast agent" (version of Sep. 16, 2015).

The effector moiety can also be a moiety having therapeutic activity. For instance, the effector can also represent a toxic reagent for a selective killing of αvβ8 carrying cells (personalized medicine).

Suitable effector moieties for use as therapeutic agents can be any active drug molecule suitable for the treatment of a medical indication or condition wherein αvβ8 integrin is upregulated or involved in the pathological mechanism in another way. Preferably it is a drug for the treatment of cancer, a virus disease or fibrosis.

More specifically, the therapeutic drug against cancer may be selected from therapeutic drugs suitable for treating cancer. For instance, the anticancer drug may be selected from the group consisting of alkylating agents, anti-metabolites, anthracyclines, plant alkaloids, topoisomerase inhibitors and other anti-tumor drugs. More specifically, the following can be mentioned: platinum based compounds, antibiotics with anti-cancer activity, anthracyclines, anthracenediones, alkylating agents, antimetabolites, Antimitotic agents, taxanes, taxoids, microtubule inhibitors, Vinca alkaloids, folate antagonists, topoisomerase inhibitors, antiestrogens, antiandrogens, aromatase inhibitors, GnRh analogs, inhibitors of 5α-reductase, bisphosphonates, a metabolic inhibitor, preferably a mTOR inhibitor; an epigenetic inhibitor, preferably a DNMT inhibitor; an anthracycline antibiotic; a camptotheca; an anthracycline; histone deacetylase (HDAC) inhibitors, proteasome inhibitors, JAK2 inhibitors, tyrosine kinase inhibitors (TKIs), PI3K inhibitors, Protein kinase inhibitors, Inhibitors of serine/threonine kinases, inhibitors of intracellular signaling, inhibitors of Ras/Raf signaling, MEK inhibitors, AKT inhibitors, inhibitors of survival signaling proteins, cyclin dependent kinase inhibitors, therapeutic monoclonal antibodies, TRAIL pathway agonists, anti-angiogenic agents, metalloproteinase inhibitors, cathepsin inhibitors, inhibitors of urokinase plasminogen activator receptor function, immunoconjugates, antibody drug conjugates, antibody fragments, bispecific antibodies, bispecific T cell engagers (BiTEs). Said anticancer drug is preferably selected from the group consisting of 5-fluorouracil, cisplatin, irinotecan hydrochloride, epirubicin, paclitaxel, docetaxel, camptothecin, doxorubicin, rapamycin, 5-azacytidine, doxorubicin irinotecan, topotecan (type 1 topoisomerase inhibitors), amsacrin, etoposide, etoposide phosphate and teniposide (topoisomerase-type 2 inhibitors); UFT, capecitabine, CPT-II, oxaliplatin, cyclophosphamide, methotrexate, navelbine, epirubicin, mitoxantrone, raloxifen, mitomycin, carboplatinum, gemcitabine, etoposide and topotecan.

The therapeutic drug may also be an antibody selected from cetuximab, panitumumab, nimotuzumab, trastuzumab, pertuzumab, rituximab, ofatumumab, veltuzumab, alemtuzumab, labetuzumab, adecatumumab, oregovomab, onartuzumab; apomab, mapatumumab, lexatumumab, conatumumab, tigatuzumab, catumaxomab, blinatumomab, ibritumomab triuxetan, tositumomab, brentuximab vedotin, gemtuzumab ozogamicin, clivatuzumab tetraxetan, pemtumomab, trastuzumab emtansine, bevacizumab, etaracizumab, volociximab, ramucirumab, aflibercept.

Yet another possibility is to use an atomic group containing a radioisotope for use in radiotherapy. Suitable radioisotopes and atomic groups containing the same as well as their applications are described in the German language Wikipedia entry "Radionuklidtherapie" (version of Sep. 16, 2015). These substances can be used in the context of the present invention by covalently bonding to the peptide compound $X^0$ of the present invention via linker L.

Such therapeutic drugs are disclosed, for instance, in "Cancer Drugs" by Judith Matray-Devoti, Chelsea House, 2006; "Physicians' Cancer Chemotherapy Drug Manual 2015" by Edward Chu, Vincent T DeVita, Jr., Jones & Bartlett Learning 2015; "Cancer Chemotherapy and Biotherapy: Principles and Practice" by Bruce A. Chabner, Dan L. Longo, Wolters Kluwer, 2011; "Drugs in Cancer Care" by Rachel Midgley, Mark R. Middleton, Andrew Dickman, David Kerr (Eds.), Oxford University Press 2013. The drugs disclosed in these books can be used as therapeutic agents when practicing the present invention. The disclosures of therapeutic drugs in these references is therefore incorporated herein.

The therapeutic drug for treatment of a virus disease may be a therapeutic drug suitable for treatment of a virus disease selected from the group consisting of antiviral drugs for suppressing HCMV proliferation such as ganciclovir, foscarnet, valganciclovir; virus neuraminidase inhibitors such as tamiflu (oseltamivir) and relenza (zanamivir); interferon-alpha; in Hepatitis B, oral anti-viral agents such as lamivudine or adefovir can be used; in Hepatitis C, ribavirin, sofosbuvir, ledipasvir, faldaprevir can be used; in influenza substances destroying influenza virus M2 protein ion channel activity such as amantadine and rimantadine. Further antiviral drugs can be used such as arbidol. Such therapeutic drugs are disclosed, for instance, in "Antiviral Drugs" by John S. Driscoll, Wiley, 2002, "Antiviral Drug Strategies" by Erik De Clercq, Wiley VCH, 2011, "Antiviral Strategies" by Hans-Georg Kräusslich, Ralf Bartenschlager, Springer 2009; "Current Trends in Antiviral Drug Development; Antivirals: latest developments and future progress" Henry Stewart Talks, 2013; "A Practical Guide to Clinical Virology" by L. R. Haaheim, John R. Pattison, Richard J. Whitley, Wiley, 2002.

The therapeutic drug for the treatment of fibrosis may be selected from therapeutic drugs suitable for the treatment of fibrosis. Such therapeutic drugs are disclosed, for instance, in "Cystic Fibrosis in the 21st Century" by Andrew Bush (Ed.), S. Karger, 2006; "Liver Fibrosis: New Insights for the Healthcare Professional: 2013 Edition" by Q. Ahton Acton, Scholarly Editions, 2013; "Idiopathic Pulmonary Fibrosis: A Comprehensive Clinical Guide" by Keith C. Meyer, Steven D. Nathan, Springer, 2014; "New Insights into the Pathogenesis and Treatment of Idiopathic Pulmonary Fibrosis: A Potential Role for Stem Cells in the Lung Parenchyma and Implications for Therapy" by M. Gharaee-Kermani et al. in Pharmaceutical Research, 2007, 24, 819-841; "Pulmonary Fibrosis: pathogenesis, etiology and regulation" by M. S. Wilson and T. A. Wynn in Mucosal Immunol. 2009, 2, 103-121. Specific preferred therapeutic drugs are preferably selected from the drugs and drug classes disclosed listed in Table II of the review article by Gharaee-Kermani et al. cited above.

In addition to the above-mentioned drugs, it is also possible to use a nucleic acid-based drug. This can be, for instance, siRNA drugs, antisense nucleic acid drugs, ribozymes, plasmid DNA for gene therapy. Suitable drugs of this type are disclosed, for instance, in "Nucleic Acid-Based Drugs" by J. P. Wong (Ed.), Future Science Ltd. 2013 and "From Nucleic Acids Sequences to Molecular Medicine" by V. A. Erdmann and J. Barciszewski (Eds.) Springer 2012. Such nucleic acid-based drug concepts can be applied to the treatment of any one of the medical indications mentioned herein, including cancer, virus diseases and fibrosis.

When attaching the effector moieties $X^8$ listed above to the linker L, it is advantageous to covalently bind the linker to a position within the effector moiety, such that the binding of the linker does not interfere with the therapeutic activity of the effector moiety.

Alternatively, the effector moiety can be an anchor group that allows to attach the compound of the invention to a surface of a greater entity such as the surface of a medical device such as a stent for prevention of proliferation and/or restenosis. The compound of the invention may also be attached to the surface of a diagnostic device to allow testing for cells and associated pathologies, wherein the αvβ8 integrin is upregulated. Yet another possible use is the attachment of the compound of the invention to a chromatography column carrier material to thereby allow isolating and/or purifying the αvβ8 integrin or biological materials containing the same. Suitable anchor groups for these possible applications are disclosed as "organic anchoring groups" in WO2007/065691 A, for instance in Embodiment 5 of this patent document.

The anchor group can also be used for attaching the compound of the invention to a liposome or other vesicle, for instance for using the compound of the present invention in drug targeting. Suitable liposome compositions and related vesicles as well as their synthesis are disclosed, for instance in WO2010/113984, EP2153820 A1, WO2008/120736, WO2014/065245, US2013/136790 A1, WO2014/025042, US2014/112979 A1, WO2004/091578 A2, WO2004/047802 A2 and on page 22 of WO 01/05810 A2 and also in "Lipid Nanoparticles: Production, Characterization and Stability" by R. Shah, Springer 2015. Attachment can be accomplished via covalent or non-covalent (such as ionic, hydrogen-bonding or hydrophobic) interactions. Suitable anchor groups can be selected taking the surface chemistry of the target surface into account. If the anchor group is to be attached to a liposome or other lipid-based vesicle, preferred interactions are ionic interactions and even more preferably hydrophobic interactions between the hydrophobic parts of the liposome-forming lipids (typically phospholipids) and the anchor group. Suitable anchor groups for this purpose are groups derived from lipid molecules wherein the lipid molecules are the same as the lipid molecules forming the liposome or are lipid molecules capable of being incorporated into the liposome lipid bilayer.

The anchor group may also be used for covalently bonding the compound of the invention to a carrier such as polymeric nanoparticles or viral nanoparticles. Suitable anchor groups therefore include functional groups that can react with functional groups present on the carrier. These can be functional groups suitable for ester or amide bond formation as well as functional groups suitable for "click chemistry" as disclosed in the Wikipedia entry "Click chemistry" (version of Feb. 20, 2017) and references cited therein. For instance, it is advantageous to use azide groups and alkyne groups for copper catalyzed [3+2]cycloadditions. This approach is described by M. L. Hovlid et al. in "Guiding plant virus particles to integrin-displaying cells" in Nanoscale 2012, 4, 3698 and in "A shortcut to high-affinity Ga-68 and Cu-64 radiopharmaceuticals: one-pot click chemistry trimerisation on the TRAP platform" by Z. Baranyai et al. in *Dalton Trans.*, 2015, 44, 11137. The synthetic approaches taken in these articles may be adapted to the use of the compound of the present invention. In a preferred embodiment of the compound of the above formula (IIa), the linker and effector together are represented by one of the moieties —(C=O)—(CH$_2$)$_n$—C≡CH and —(C=O)—(CH$_2$CH$_2$O)$_m$—C≡CH, with n and m being individually selected from the group 1, 2, 3, 4, 5, 6, 7, 8, 9 and 10, which is bonded to the terminal amino group of the N-methyl-lysine residue of X$^3$ by amide bond formation or to the C-4 atom of proline of X$^3$. It is similarly preferred if an azide group is bonded to one of these residues, for instance via amide bonding of one of the following moieties —(C=O)—(CH$_2$)$_n$—N$_3$ and —(C=O)—(CH$_2$CH$_2$O)$_m$—N$_3$, with n and m being again selected from the group 1, 2, 3, 4, 5, 6, 7, 8, 9 and 10. Of course, the above-mentioned Click chemistry may also be used for forming a 5-membered N-containing heterocyclic group as mentioned in Section 4.3.2 above as a linker element for attaching other effector moieties as listed above. The above-mentioned residues Pro-R$^{x3}$, N-Me-Lys-R$^{x4}$ may be used as suitable building blocks.

Attaching the compound of the invention to a liposome or other vesicle may allow to use the compound of the invention as a targeting moiety for specifically delivering the liposome or other vesicle and their respective contents to a target cell. The resulting increase in local concentration in the vicinity of the target cell may permit to accomplish increased therapeutic efficacy without concomitant increase in side effects. It may even be possible to accomplish internalization of the active agent by the target cell via active transport mechanisms in analogy to S. Lucie et al. "Clustering and Internalization of Integrin α v β 3 With a Tetrameric RGD-synthetic Peptide" in *Molecular Therapy* 2009, 17, 837-843.

The effector moiety together with the linker may also be suitably selected to create a functional chimeric T cell antigen receptor that can be used for immunotherapy applications e.g. in the treatment of cancer. Suitable methods and materials may be adapted from "Conversion of a tumor-binding peptide identified by phage display to a functional chimeric T cell antigen receptor" by C. R. J. Pameijer et al. in Cancer Gene Therapy 2007, 14, 91-97.

The effector moiety encompasses not only the active atom or atom group (e.g. a radioactive atom in case of radiolabeling) but also the additional atoms or atomic groups used for bonding of the active atom or atomic group. For instance, the effector moiety may encompass the ligands and chelators shown in FIGS. 4 and 7 of "Ligands for Mapping αvβ3-Integrin Expression in Vivo" by M. Schottelius et al. in *Acc. Chem. Res.* 2009, 42, 969-980 (together with suitably selected active atoms) and also the complexes of active atom and ligand as shown in FIGS. 4, 6, 10, 11, 12 and 14 of this article. In case of doubt, if it is not clear which atoms form part of the linker and which atoms form part of the effector moiety, the effector moiety is to be understood as comprising only the active atom or atomic group, the smallest atomic group (functional group) required for bonding the active atom or atomic group and the atom or atomic group (functional group) required for bonding the effector moiety to a terminus of the linker.

4.4. Synthesis of Compounds of the Invention

The compounds of the invention can be synthesized using standard peptide methodology such as solid phase peptide synthesis using Fmoc as a protective group. The available techniques are described for instance in J. Chatterjee, B. Laufer, H. Kessler, Nat. Protoc. 2012, 7, 432-444.

Cyclization of the peptide can be effected using standard techniques. For instance, cyclization can be accomplished on the solid support or in solution using HBTU/HOBt/DIEA, PyBop/DIEA or PyClock/DIEA reagents. The available cyclization methods are described for instance in J.

Chatterjee, B. Laufer, H. Kessler, *Nat. Protoc.* 2012, 7, 432-444 and references cited therein.

4.5. Pharmaceutical Compositions

The compounds of the present invention can be formulated with excipients to yield pharmaceutical compositions. These can be pharmaceutical compositions for oral or parenteral administration including for instance intravenous administration, intramuscular administration, transdermal administration, transmucosal administration, pulmonary administration, intranasal administration, as well as any other administration form that allows to present the compound of the present invention to the target cells wherein the αvβ8 integrin is upregulated or involved in the pathological mechanism in another way.

Pharmaceutical compositions for parenteral administration including intravenous administration, intramuscular administration, transdermal administration, transmucosal administration, pulmonary administration, and intranasal administration can be made using the methods and materials disclosed in "Pharmaceutical Dosage Forms: Parenteral Medications" by Kenneth E. Avis, Herbert A. Lieberman, Leon Lachman, M. Dekker, 1993 and in "Remington The Science and Practice of Pharmacy" Edited by Allen, Loyd V., Jr, Pharmaceutical Press, $22^{nd}$ Ed. 2012; "Pharmazeutische Technologie: Moderne Arzneiformen" by R. H. Müller and G. E. Hildebrand, W V G, $2^{nd}$ Ed. 1998, "Arzneiformen richtig anwenden" by Kircher, Wolfgang, Deutscher Apotheker Verlag, $3^{rd}$ Ed. 2007; "Lehrbuch der Pharmazeutischen Technologie: Mit einer Einführung in die Biopharmazie" by Kurt H. Bauer, Karl-Heinz Fromming, Claus Führer, W V G 2012; "Pharmazeutische Technologie: Fir Studium und Beruf (Wissen und Praxis)" by Alfred Fahr, Rudolf Voigt, Deutscher Apotheker Verlag, $12^{th}$ Ed. 2015.

Pharmaceutical compositions for oral administration can be made using the methods and materials disclosed in Pharmaceutical Dosage Forms: Tablets, Second Edition, Volume 3 by Herbert A. Lieberman et al., Taylor & Francis 1990; "Die Tablette" by A. Bauer-Brandl, W. A. Ritschel, Editio Cantor Verlag, $3^{rd}$ Ed. 2011 as well as the documents cited above in relation to parenteral administration forms.

Further available formulation strategies are described and discussed, for instance, in Ther. Deliv. 2015 February; 6(2):149-63 "Challenges in the delivery of peptide drugs: an industry perspective" by Lewis AL1, Richard J.; Biotechnol. Adv. 2015 Feb. 14. pii: S0734-9750(15)00023-3. doi: 10.1016/j.biotechadv.2015.01.010. [Epub ahead of print] *"Recent advances in topical delivery of proteins and peptides mediated by soft matter nanocarriers"* by Witting, Obst, Friess, Hedtrich; Protein Pept Lett. 2014; 21(11):1087-101, *"Novel non-invasive protein and peptide drug delivery approaches"* by Wallis L, Kleynhans E, Toit T D, Gouws C, Steyn D, Steenekamp J, Viljoen J, Hamman J; Protein Pept Lett. 2014; 21(11): 1102-20, *"Recent advances in protein and Peptide drug delivery: a special emphasis on polymeric nanoparticles"* by Patel A, Patel M, Yang X, Mitra A K; and Curr Drug Deliv. 2007 April; 4(2):141-51, *"Recent advances in protein and peptide drug delivery systems"* by Malik DK1, Baboota S, Ahuja A, Hasan S, Ali J; and ACS Symposium Series Vol. 567 *"Formulation and Delivery of Proteins and Peptides"* by American Chemical Society 1994, Cleland J L and Langer R (Eds.).

4.6. Use as Therapeutic Drug

4.6.1. Treatment of Cancer

Due to their highly active and selective binding to αvβ8 integrin, the compounds of the present invention can be used for treating those types of cancer, wherein αvβ8 integrin is upregulated or otherwise involved in the pathological mechanism. Such types of cancer include squamous cell carcinomas, pancreatic tumors and tumors of the ovaries as well as lung cancer, prostate cancer [Mertens-Walker et al. The tumour-promoting receptor tyrosine kinase, EphB4, regulates expression of Integrin-β8 in prostate cancer cells. BMC Cancer 15, Art. No. 164 (2015). DOI: 10.1186/s12885-015-1164-6], colon cancer, glioblastoma, lymph node metastasis [Kawashima, A. et al. Expression of alphav integrin family in gastric carcinomas: increased alphavbeta6 is associated with lymph node metastasis. Pathol Res Pract. 2003; 199(2):57-64] and breast cancer. Further specific cancer types that may be treated with the compounds of the present invention are head and neck squamous cell carcinoma such as oral squamous cell carcinoma, laryngeal squamous cell carcinoma, oropharyngeal squamous cell carcinoma, nasopharyngeal squamous cell carcinoma, hypopharyngeal squamous cell carcinoma. Other types of cancer that can be treated with the compounds of the invention include specifically non-small cell lung cancer (NSCLC) and gastric cancer. Such cancers may be treated in any mammal and preferably in humans.

The compounds of the present invention may be administered to the patient for instance by intravenous, transmucosal, transdermal, intranasal administration. Suitable dosages may be in the range of 0.1 to 2000 mg/day, preferably 1 to 1000 mg/day. The compounds of the present invention may be administered once daily, twice a day, three times a day, etc. for any period of time, wherein multiple periods of time may be interrupted by one or more periods of time where the compounds of the present invention are not administered.

The compounds of the present invention may also be used as a component in combination therapy. They may be combined with one or more other therapeutic agents effective in the treatment of cancer such as the therapeutic agents listed above and/or below. Such combination therapy may be carried out by simultaneously or sequentially administering the two or more therapeutic agents.

The compounds of the present invention may also be used in personalized medicine therapeutic approaches. It is for instance possible to first determine the pattern of expression of the different integrin subtypes in the patient and then to administer a compound of the present invention for therapeutic purposes if the expression of the αvβ8 integrin is upregulated. Alternatively, it is a possibility to confirm the expression of the αvβ8 integrin on the surface of the patient's tumor cells (e.g. with the imaging methods described herein). The administration of a therapeutic agent that is selective for cancer cells carrying the αvβ8 integrin may then follow once the presence of the αvβ8 integrin on the surface of the tumor cells has been confirmed. Of course, it is similarly possible to use alternative substances that selectively bind to other integrin subtypes if such other integrin subtypes should be upregulated. Such an approach avoids treatment with drugs which cannot be efficient when the receptor is not expressed. Often personalized medicine refers only to the DNA/RNA mutations, but the cancer types are not fully characterized by the genes but more by the expressed proteins. Personalizing the therapeutic approach based on the protein expression pattern, as described herein, is therefore a promising approach.

4.6.2. Treatment of Fibrosis

The compounds of the present invention may also be used for treating fibrosis and in particular where αvβ8 integrin is upregulated, e.g. among others, pulmonary fibrosis, cystic fibrobis, idiopatic pulmonary fibrosis, endomyocardial fibrosis, Crohn's disease, and arthofibrosis. In addition, they may also be useful for enhancing wound healing [Neurohr, C., Nishimura, S. L. & Sheppard, D. Activation of Transforming Growth Factor-β by the Integrin αvβ8 Delays Epithelial Wound Closure, Cell Mol. Biol. 35, 252-259 (2006). DOI: 10.1165/rcmb.2006-0013OC].

The compounds of the present invention may be used for the treatment of fibrosis by any suitable administration form including intravenous, transmucosal, pulmonary, and intranasal administration. Dosages and administration schemes can be the same as specified above for the treatment of cancer. Combination therapy is also possible, wherein the one or more other therapeutic agents is selected from other therapeutic agents suitable for the treatment of fibrosis, for instance as cited above by cross-reference to the review article by Gharaee-Kermani et al. The compounds of the present invention as well as the one or more other therapeutic agents can be administered simultaneously or sequentially.

4.6.3. Treatment of Virus Diseases

The αvβ8 integrin is used by certain types of viruses to enter the host cells. These are, for instance, Foot-and-Mouth-Disease Virus, human parechovirus 1 and coxsackievirus A9, which is causative for meningitis and other medical conditions. The compounds of the present invention can be used for treating such virus diseases by blocking entry of the virus into the host cell [Gianni, T., Massaro, R. & Campadelli-Fiume, G. Dissociation of HSV gL from gH by alpha v beta 6-or alpha v beta 8-integrin promotes gH activation and virus entry. Proc. Nat. Acad. Sci. 112, 3901-3910 (2015). DOI: 0.1073/pnas.1506846112].

The compounds of the present invention may be used for the treatment of such virus diseases by any suitable administration form including intravenous, transmucosal, pulmonary, intranasal and intramuscular administration. Dosage and administration schemes can be the same as described above with respect to the treatment of cancer. Combination therapy involving the compounds of the present invention as well as one or more other antiviral drugs is feasible, too. In this case, the compounds of the present invention and the one or more other antiviral drugs, e.g. as listed above, can be administered simultaneously or sequentially.

4.6.4. Treatment of Other Medical Conditions

In addition to the above-mentioned medical conditions, the compounds of the present invention are also suitable for the treatment of medical conditions and selected from cornea dysfunctions, interstitial lung disease, thrombosis, myocardial infarction, coronary myocardial disease, arteriosclerosis, osteoporosis, inflammation, and psoriasis.

Suitable dosages, administration forms, administration schemes, patient groups, etc. can be identified by the person skilled in the art relying on common general knowledge and routine procedure.

4.7. Use as Diagnostic Agent

Compounds of the present invention are also suitable for use as diagnostic agent. In this case, compounds of the present invention of general formula (II) are advantageously used, wherein the effector moiety $X^8$ is a labeling group as described above. Depending on the chosen analytical/diagnostic method to be used, a suitable labeling group is selected. The chosen analytical/diagnostic method also determines the dosage, form and timing of the administration of the diagnostic agent of the present invention.

The diagnostic agents of the present invention are suitable for virtually any analytical/diagnostic method that involves the use of diagnostic agents. The diagnostic agents of the present invention are particularly suitable for imaging methods such as fluorescence-based imaging, positron emission tomography (PET), single-photon emission computed tomography (SPECT), optical imaging or magnetic resonance imaging (MRI), X-ray based CT imaging, scintigraphy, ultrasonography and thermography.

4.8. Use for Drug Targeting

The compounds of the present invention may also be used as targeting agents together with other therapeutic agents and suitable carriers. Typically, the other therapeutic agent is contained within a suitable carrier whereas the compounds of the present invention are attached to the surface of the carrier. Selective binding of the compounds of the present invention to the αvβ8 integrin gives rise to an increased local concentration of the targeting complex including the other therapeutic agent in the vicinity of the target cells. This local increase in concentration of the other therapeutic agent may favorably improve the ratio of beneficial therapeutic effects to undesired side effects.

Suitable carriers for drug targeting may be selected from liposomes, nanoparticles including polymeric nanoparticles and viral nanoparticles, micelles, microspheres made of biodegradable polymer, etc. Materials and methods that can be used in the present invention are discussed in US2015/202316 A1, US2014/178296 A1, CN103446053 A, CN103520207 A, TW201121573 A, "Guiding plant virus particles to integrin-displaying cells" by M. L. Hovlid et al. in Nanoscale 2012, 4, 3698, "Solid-phase-assisted synthesis of targeting peptide-PEG-oligo(ethane amino)amides for receptor-mediated gene delivery" by I. Martin et al., *Org. Biomol. Chem.* 2012, 10, 3258 and "Advanced targeted therapies in cancer: Drug nanocarriers, the future of chemotherapy" by Pérez-Herrero E., Fernández-Medarde A., Eur. *J. Pharm. Biopharm.* 2015, 93, 52-79 and references cited therein. Of course, it will be necessary to substitute the targeting moieties and possibly also drug agents described in these documents by the compound of the present invention. Depending on the intended use, it may also be appropriate to replace the therapeutic agents and/or imaging agents of these documents by the therapeutic agents and/or imaging agents appropriate for the intended use.

The other therapeutic agent to be targeted is not particularly limited. It is, of course, reasonable to use the drug targeting approach for treating a medical condition, wherein αvβ8 integrin is upregulated or otherwise involved in the pathological mechanism. Hence, the other therapeutic agent is advantageously selected among therapeutic agents that are suitable for treating a medical condition of this type including especially the drugs disclosed above.

Suitable drug targeting concepts are described by U. Kiran Marelli et al. in "Tumor targeting via integrin ligands" in Frontiers in Oncology, 2013, 3, 1-12. The drug targeting concepts and especially the carrier systems and drugs disclosed in this review article and the documents cited therein may also be used in the context of the present invention.

4.9. Use for Biomolecular Research

The compounds of the present invention may also be used for obtaining additional information on molecular mechanisms underlying particular medical conditions of interest, as ligands for purifying αvβ8 integrin in affinity chromatography columns, or for FACS analysis. The compounds of the present invention can also be used for investigating individual integrin functions and/or cross talk between different integrin types. The present invention thus pertains also to devices for use in these techniques, wherein the modified compound of the present invention (or its salts or esters) is bonded covalently or non-covalently via effector moiety $X^8$ to the respective devices such as a chromatography stationary phase support material. When using the compounds of the present invention in FACS analysis, it is appropriate to use the compound of the invention in the form of a modified compound, wherein the effector moiety $X^8$ is or contains a fluorescence label.

5. EXAMPLES

5.1. General Information

Chemicals: All reagents and solvents were obtained from commercial suppliers and used without further purification.

Chromatography: Analytical HPLC-ESI-MS was performed on a Hewlett-Packard Series HP 1100 equipped with a Finnigan LCQ mass spectrometer using a YMC-Hydrosphere C18 column (12 nm pore size, 3 μm particle size, 125 mm×2.1 mm) or YMC-Octyl C8 column (20 nm pore size, 5 μm particle size, 250 mm×2.1 mm) and $H_2O$ (0.1% v/v formic acid)/MeCN (0.1% v/v formic acid) as eluents. Semi-preparative HPLC was performed using a Beckmann instrument (system gold, solvent delivery module 126, UV detector 166), an YMC ODS-A column (20×250 mm, 5 μm), flow rate: 8 mL/min, linear gradients of $H_2O$ (0.1% v/v TFA) and MeCN (0.1% v/v TFA).

NMR: $^1$H-NMR and $^{13}$C NMR spectra were recorded at 295 K on a 500 MHz Bruker DMX, 360 MHz Bruker AV or a 250 MHz Bruker AV spectrometer (Bruker, Karlsruhe, Germany). Chemical shifts (δ) are given in parts per million (ppm). The following solvent peaks were used as internal standards: DMSO-$d_5$: 2.50 ppm ($^1$H-NMR) and 39.52 ppm ($^{13}$C-NMR); CHCl$_3$: 7.26 ppm ($^1$H-NMR) and 77.16 ppm ($^{13}$C-NMR). [Gottlieb, H. E.; Kotlyar, V.; Nudelman, A. NMR Chemical Shifts of Common Laboratory Solvents as Trace Impurities. *J. Org. Chem.* 1997, 62, 7512-7515.]

5.2. Example 1: Synthesis of Peptide Compounds

Cyclic peptides were prepared according to the standard Fmoc-Solid Phase Peptide Synthesis (Fmoc-SPPS) using a tritylchloride polystyrene (TCP) resin followed by cyclization in solution [D. Heckmann, H. Kessler, Design and Chemical Synthesis of Integrin Ligands, *Methods in Enzymology* 2007, 426, 463-503]. N-Methylation was performed on a resin according to the previously reported method [J. Chatterjee, B. Laufer, H. Kessler, Synthesis of N-methylated cyclic peptides, Nature protocols, 2012, 7 (3), 432-444] with one exception: N-Nosyl protection was performed in dichloromethane (DCM) instead of N-methylpyrrolidine (NMP).

Following acid labile groups were used for protection of side-chains of amino acids: Pbf for Arginine; tert-butyl (tBu) for Threonine, Aspartic acid, and Tyrosine; tert-butyloxycarbonyl (Boc) for Lysine and Tryptophan. They were removed using a mixture of trifluoroacetic acid (TFA)/DCM/triisopropylsilane (TIPS)/water (80:10:5:5) for 1.5 h at r.t. Dde protection of side-chain of Lysine was used in the case of large synthesis of cyclic peptide 9 and its functionalized derivatives 11 and 12. The selective deprotection of Dde was performed using 2 vol.-% solution of hydrazine hydrate in dimethylformamide (DMF) for 30 min at r.t. without any effect on Pbf or tBu protective groups.

5.3. Example 2: Integrin Binding Assay

The activity and selectivity of integrin ligands were determined by a solid-phase binding assay according to the previously reported protocols using coated extracellular matrix proteins and soluble integrins: Fibronectin (Fn) for α5β1, latent activating protein (LAP) for αvβ6 and αvβ8, Vitronectin (Vn) for αvβ3 and αvβ5, Fibrinogen (Fbg) for αIIbβ3.

The results obtained in the integrin binding assay are summarized in Table 1 below.

TABLE 1

| Integrin binding affinities of tested compounds | | | |
|---|---|---|---|
| Cpd. | Sequence | αvβ6 [nM] | αvβ8 [nM] |
| 1 | Cyclo-(Arg-Gly-Asp-Leu-D-Pro-Pro-Ala-Leu) | 84 | 1.4 |
| 2 | Cyclo-(Arg-Gly-Asp-Leu-D-Pro-Pro-Gly-Leu) | 210 | 0.93 |
| 3 | Cyclo-(Arg-Gly-Asp-Leu-D-Pro-Pro-Ser-Leu) | 187 | 12.5 |
| 4 | Cyclo-(Arg-Gly-Asp-Leu-D-Pro-Pro-Ala-Tyr) | 156 | 1.1 |
| 5 | Cyclo-(Arg-Gly-Asp-Leu-D-Pro-Pro-Ala-His) | 171 | 2.2 |
| 6 | Cyclo-(Arg-Gly-Asp-Leu-(N-Me-D-Phe)-Pro-Ala-Leu) | 139 | 9.4 |
| 7 | Cyclo-(Arg-Gly-Asp-Leu-D-Pro-Pro-Ala-Leu) | 32 | 1.31 |
| 8 | Cyclo-(Arg-Gly-Asp-Leu-D-Pro-(N-Me-Lys)-Gly-Leu) | 201 | 6.5 |
| 9 | Cyclo-(Arg-Gly-Asp-Leu-D-Pro-(N-Me-Lys(Ac))-Gly-Leu) | 201 | 6.0 |
| 10 | Cyclo-(Arg-Gly-Asp-Leu-D-Pro-Pro-Ala-Ala) | 114 | 8.1 |
| 11 | Cyclo-(Arg-Gly-Asp-Leu-D-Pro-(N-Me-Lys-pentyne)-Gly-Leu) | 41 | 1.7 |
| 12 | Cyclo-(Arg-Gly-Asp-Leu-D-Pro-(Pro-4-NH-hexyne)-Gly-Leu) | 217 | 8.8 |
| 13 | Cyclo-(Arg-Gly-Asp-Leu-D-Pro-Pro-Ala-Phe) | 81 | 1.83 |

The following compounds were used as internal standards: Cilengitide, c(-RGDf(NMe)V-) (αvβ3—0.54 nM, α5β1—8 nM),[3] linear peptide RTDLDSLRT[4] (αvβ6—33 nM; αvβ8—100 nM) and tirofiban[5] (αIIbβ3—1.2 nM).

A complete profile of selected cyclic peptides is provided in Table 2.

TABLE 2

| Cpd. | Amino acid sequence | αvβ6, $IC_{50}$ [nM] | αvβ3, $IC_{50}$ [nM] | α5β1, $IC_{50}$ [nM] | αvβ8, $IC_{50}$ [nM] | αIIbβ3, $IC_{50}$ [nM] | αvβ5, $IC_{50}$ [nM] |
|---|---|---|---|---|---|---|---|
| 2 | c(RGDLpPGL) | 210 | >1000 | >1000 | 0.93 | >1000 | >1000 |
| 8 | c(RGDLp(NMe)KGL) | 201 | >1000 | >1000 | 6.5 | >1000 | >1000 |
| 9 | c(RGDLp(NMe)K(Ac)GL) | 201 | 423 | >1000 | 6.0 | >1000 | >1000 |

In yet further experiments, the binding profile of compounds of the invention provided with effector moieties was investigated. In particular, the influence of different linkers and of trimerization was investigated. The above-mentioned compound 9 was modified at the ω amino group with the Bodipy-fluorescence dye (BDPFL) using different linkers as shown below. The resulting binding profiles are shown in Table 3 below.

TABLE 3

| Compound | Amino acid sequence | αvβ8, $IC_{50}$ [nM] | αvβ6, $IC_{50}$ [nM] | αvβ3, $IC_{50}$ [nM] | αvβ5, $IC_{50}$ [nM] | α5β1, $IC_{50}$ [nM] | αIIbβ3, $IC_{50}$ [nM] |
|---|---|---|---|---|---|---|---|
| 9a | 9-BDPFL | 0.66 | 94 (195) | 676 (*80*) | >10000 | 1469 | n.d. |
| 9b | 9-Ahx-BDPFL | 0.87 | 55 (35) | 239 | >10000 | >1000 | >1000 |
| 9c | 9-Ahx-Ahx-BDPFL | 1.52 | 64 | 500 | n.d. | n.d. | n.d. |
| 9d | 9-(PEG)$_5$-BDPFL | 1.25 | 247 | *98* | >10000 | *95* | n.d. |
| 9e | 9-G(P)$_3$G-BDPFL | 2.07 | 247 | *585* | >10000 | *979* | n.d. |
| 9f | 9- G(P)$_6$G-BDPFL | 7.98 | 453 | *42* | >10000 | *782* | n.d. |
| 10 | Ahx-BDPFL | 9810 | >10000 | >10000 | >10000 | >10000 | n.d. |
| 11 | c(GLRVDLp(NMe)K)-Ahx-BDPFL | 1124 | >10000 | >10000 | n.d. | n.d. | n.d. |
| 12 | c(RGDfK) [a] | 5200 | 55 | 2.25 | 340 | 141 | >10000 |
| 13 | c(RGDfK)-Ahx-BDPFL | 258 | 7.8 | 2.55 | n.d. | n.d. | n.d. |

PEG: structure corresponding to polyethylene glycol,
Ahx: structure derived from 6-amino hexanoic acid
P: structure derived from proline
Values in italics are subject to a greater error/uncertainty A comparison of the binding profile shown for compound 9 and modified compounds 9a to 9e reveals that the binding activity to αvβ8 could be increased for these linkers. Compound 9f, on the other hand, showed a reduced binding activity to αvβ8. Compounds 10 to 13 are comparative compounds demonstrating that the dye-linker-conjugate alone shows no binding activity (compound 10), that a minor replacement in the peptide sequence (Gly replaced by Val) significantly reduces binding activity (compound 11) and that compounds known to strongly bind to αvβ3 do not show strong binding to αvβ8, irrespective whether they are provided with an effector moiety (compound 13) or not (compound 12).

Further experiments with compound 9, but modified with the Ga-TRAP effector moiety demonstrate that trimerization can increase binding activity. The results of these experiments are summarized in Table 4 below.

TABLE 4

| Compound | Amino acid sequence | αvβ8, IC$_{50}$ [nM] | αvβ6, IC$_{50}$ [nM] | αvβ3, IC$_{50}$ [nM] | αvβ5, IC$_{50}$ [nM] | α5β1, IC$_{50}$ [nM] | αIIbβ3, IC$_{50}$ [nM] |
|---|---|---|---|---|---|---|---|
| 14 | Ga-TRAP-9 (Monomer) | 33 | 357 | 624 | >1000 | >1000 | >1000 |
| 15 | Ga-TRAP-9 (Trimer) | 0.89 | 67 | n.d. | >1000 | >1000 | >1000 |

It is noteworthy that trimerization not only improved binding to αvβ8, but that it additionally increased binding specificity since the binding to other receptors including αvβ6 did not increase to the same extent.

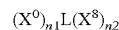

The invention claimed is:

1. A compound represented by the following general formula (I):

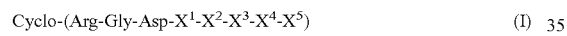

wherein the variables groups $X^1$ to $X^5$ have the following meanings $X^1$: Leu, Ile, Nle, Val, Tyr, Phe
$X^2$: D-Pro, N-Me-D-Phe
$X^3$: Pro, N-Me-amino acid
$X^4$: Gly, Ala, Ser, Thr
$X^5$: Leu, Ala, Tyr, His, Ile, Nle, Val, Phe or pharmaceutically acceptable salts, esters, solvates, polymorphs or modified forms thereof represented by the following general formula (II):

$$(X^0)_{n1}L(X^8)_{n2}$$

wherein $X^0$ represents the compound of the general formula (I) as specified above (excluding one hydrogen atom to allow bonding to the linker), L represents a linker, $X^8$ represents an effector moiety and wherein n1 and n2 are each independently selected from the range of 1 to 5, wherein n1+n2 represents the number of valencies of the linker.

2. The compound or pharmaceutically acceptable salts, esters, solvates, polymorphs or modified forms thereof according to claim 1, wherein the variable group $X^3$ has the following specific meanings $X^3$: Pro, N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$ wherein Pro-R$^{x3}$ represents a proline residue or azaproline residue that is functionalized at the C-3, C-4 or C-5 carbon atom with a functional group selected from —NH$_2$, —OH, —NH—Ac, —NH-L4-R4, wherein L4 is selected from the group consisting of covalent bond, —C(O)—, and —C(O)—O—, and wherein R4 is selected from the group consisting of —(CH$_2$)n-C≡CH and —(CH$_2$)n-N$_3$ with n=0, 1, 2, 3, 4, 5, 6, 7, 8, 9, or 10, wherein Lys-R$^{x4}$ represents a residue derived from a lysine residue, wherein the ω-amino nitrogen atom carries a group of the formula -L4-R4, wherein L4 is selected from the group consisting of covalent bond, —C(O)—, and —C(O)—O—, and wherein R4 is selected from the group consisting of —(CH$_2$)$_n$—C≡CH and —(CH$_2$)$_n$—N$_3$ with n=0, 1, 2, 3, 4, 5, 6, 7, 8, 9, or 10, wherein N-Me-Lyy-R$^{x4}$ is a residue derived from N-Me-Lyy, wherein the side chain amino nitrogen atom carries a group of the formula -L4-R4, wherein L4 is selected from the group consisting of covalent bond, —C(O)—, and —C(O)—O—, and wherein R4 is selected from the group consisting of —(CH$_2$)$_n$—C≡CH, and —(CH$_2$)$_n$—N$_3$ with n=0, 1, 2, 3, 4, 5, 6, 7, 8, 9 or 10;

wherein N-Me-Lyy is a residue of the formula: —N(CH$_3$)—CH(R$^{Lyy}$)—CO—;

wherein R$^{Lyy}$ represents —(CH$_2$)$_y$—NH$_2$ and y=1, 2, 3, 5, 6, 7, 8, 9 or 10;

wherein N-Me-Gln-R$^{x4}$ is a residue derived from N-Me-Gln, wherein the nitrogen atom of the side chain carries a group of the formula -L4-R4, wherein L4 is selected from the group consisting of covalent bond, —C(O)—, and —C(O)—O—, and wherein R4 is selected from the group consisting of —(CH$_2$)$_n$—C≡CH and —(CH$_2$)$_n$—N$_3$ with n=0, 1, 2, 3, 4, 5, 6, 7, 8, 9 or 10;

wherein N-Me-Gln is N-methyl-glutamine;

wherein N-Me-Gyy-R$^{x4}$ represents a residue derived from N-Me-Gyy, wherein the nitrogen atom of the side chain carries a group of the formula -L4-R4, wherein L4 is selected from the group consisting of covalent bond, —C(O)—, and —C(O)—O—, and wherein R4 is selected from the group consisting of —(CH$_2$)$_n$—C≡CH and —(CH$_2$)$_n$—N$_3$ with n=0, 1, 2, 3, 4, 5, 6, 7, 8, 9 or 10;

wherein N-Me-Gyy is a residue of the formula: —N(CH$_3$)—CH(R$^{Gyy}$)—CO—, wherein R$^{Gyy}$ represents —(CH$_2$)$_y$—CO—NH$_2$ with y=1, 3, 5, 6, 7, 8, 9 or 10; and wherein the remaining variable groups X$^1$ to X$^5$ have the same meanings as specified in claim 1.

3. The compound or pharmaceutically acceptable salts, esters, solvates, polymorphs or modified forms thereof according to claim 1, wherein the compound is selected from:

Cyclo-(Arg-Gly-Asp-Leu-D-Pro-Pro-Ala-Leu)
Cyclo-(Arg-Gly-Asp-Leu-D-Pro-Pro-Gly-Leu)
Cyclo-(Arg-Gly-Asp-Leu-D-Pro-Pro-Ser-Leu)
Cyclo-(Arg-Gly-Asp-Leu-D-Pro-Pro-Ala-Tyr)
Cyclo-(Arg-Gly-Asp-Leu-D-Pro-Pro-Ala-His)
Cyclo-(Arg-Gly-Asp-Leu-(N-Me-D-Phe)-Pro-Ala-Leu)
Cyclo-(Arg-Gly-Asp-Leu-D-Pro-Pro-Ala-Leu)
Cyclo-(Arg-Gly-Asp-Leu-D-Pro-(N-Me-Lys)-Gly-Leu)
Cyclo-(Arg-Gly-Asp-Leu-D-Pro-(N-Me-Lys(Ac))-Gly-Leu)
Cyclo-(Arg-Gly-Asp-Leu-D-Pro-Pro-Ala-Ala)
Cyclo-(Arg-Gly-Asp-Leu-D-Pro-(N-Me-Lys-pentyne)-Gly-Leu)
Cyclo-(Arg-Gly-Asp-Leu-D-Pro-(Pro-4-NH-hexyne)-Gly-Leu)
Cyclo-(Arg-Gly-Asp-Leu-D-Pro-Pro-Ala-Phe).

4. The compound of claim 1, wherein X$^3$ is selected from the group consisting of N-Me-Lys, N-Me-Lys(Ac); Pro-R$^{x3}$, N-Me-Lys-R$^{x4}$, N-Me-Lyy, N-Me-Lyy-R$^{x4}$, N-Me-Gln, N-Me-Gln-R$^{x4}$, N-Me-Gyy, N-Me-Gyy-R$^{x4}$, wherein Pro-R$^{x3}$ represents a proline or aza-proline residue that carries at the atom in positions 3, 4 or 5, according to the normal proline numbering scheme, a functional group selected from —NH$_2$, —OH, —NH—Ac, —NH-L4-R4, wherein N-Me-Lys-R$^{x4}$ represents an N-methyl lysine residue, wherein the ω-amino nitrogen atom carries a group of the formula -L4-R4, wherein N-Me-Lyy represents a residue represented by the following general formula: —N(CH$_3$)—CH(R$^{Lyy}$)—CO—, wherein R$^{Lyy}$ represents —(CH$_2$)$_y$—NH$_2$ with y=1, 2, 3, 5, 6, 7, 8, 9 or 10, wherein N-Me-Lyy-R$^{x4}$ represents a residue derived from N-Me-Lyy, wherein the side chain amino nitrogen atom carries a group of the formula -L4-R4, wherein N-Me-Gln-R$^{x4}$ is a residue derived from N-Me-Gln, wherein the nitrogen atom of the side chain carries a group of the formula -L4-R4, wherein N-Me-Gyy represents a residue represented by the following general formula: —N(CH$_3$)—CH(R$^{Gyy}$)—CO—, wherein R$^{Gyy}$ represents —(CH$_2$)$_y$—CO—NH$_2$ with y=1, 3, 5, 6, 7, 8, 9 or 10, wherein N-Me-Gyy-R$^{x4}$ represents a residue derived from N-Me-Gyy, wherein the nitrogen atom of the side chain carries a group of the formula -L4-R4, wherein in all of the above formulae L4 is selected from the group consisting of covalent bond, —C(O)—, and —C(O)—O—, and wherein R4 is selected from the group consisting of —(CH$_2$)$_n$—C≡CH and —(CH$_2$)$_n$—N$_3$ with n=0, 1, 2, 3, 4, 5, 6, 7, 8, 9 or 10, or wherein the sub-sequence -X$^2$-X$^3$- represents a β-turn mimetic differing from the meanings above.

5. The compound of claim 1, wherein n1+n2 is in the range of from 2 to 5.

6. The modified compound according to claim 1, wherein the linker is selected from the group consisting of ethylene glycol, polyethylene glycol (PEG), propylene glycol, polypropylene glycol (PPG), amino acids, oligopeptides, saccharides and oligosaccharides and combinations thereof.

7. The modified compound according to claim 1, wherein the effector moiety X$^8$ is selected from
(i) an atomic group suitable for labelling the compound of claim 1,
(ii) an atomic group having therapeutic activity, or
(iii) an atomic group suitable for use as an anchor group to make the compound suitable for covalent or non-covalent bonding to other entities, wherein the other entities are selected from the group consisting of a medical device, a diagnostic device, a chromatography column carrier material, a vesicle, and a carrier.

8. The modified compound according to claim 1, wherein the linker is attached to the compound of general formula (I) via a side chain of one of the variable group X$^3$.

9. The modified compound according to claim 7, wherein the effector moiety X$^8$ is selected from
(i) an atomic group suitable for labelling the compound of claim 1, which is selected from the group consisting of a labelling group for use in fluorescence labelling, positron emission tomography (PET), single-photon emission computed tomography (SPECT), optical imaging and magnetic resonance imaging (MRI); or
(ii) an atomic group having therapeutic activity for the treatment of cancer, a virus disease or fibrosis.

10. A pharmaceutical composition comprising a compound or pharmaceutically acceptable salts, esters, solvates, polymorphs or modified forms thereof according to claim 1 and one or more pharmaceutically acceptable excipients.

11. The pharmaceutical composition according to claim 10, wherein the pharmaceutical composition is formulated to be administered by intravenous administration, intramuscular administration, transdermal administration, transmucosal administration, pulmonary administration, intranasal administration, and oral administration.

12. A pharmaceutical composition comprising a component obtainable by covalently bonding a compound or pharmaceutically acceptable salts, esters, solvates, polymorphs or modified forms thereof according to claim 1 via the effector moiety X$^8$ to a larger entity, wherein the larger entity is a carrier.

13. The pharmaceutical composition of claim 12, wherein the larger entity is a virus capsid.

14. The pharmaceutical composition according to claim 12, wherein the pharmaceutical composition is formulated to be administered by intravenous administration, intramuscular administration, transdermal administration, transmucosal administration, pulmonary administration, intranasal administration, and oral administration.

15. A device obtainable by covalently or non-covalently bonding the modified forms of formula (I), according to claim 1, represented by formula (II), or pharmaceutically acceptable salts, esters, solvates, or polymorphs thereof, via the effector moiety X$^8$ to a larger entity, wherein the larger entity is a medical device, a diagnostic device, an analytical device, or a device for purifying or separating chemical or biological substances.

16. The device of claim 15, wherein the larger entity is a stent.

17. A method for treatment of a medical condition in a subject, wherein αvβ8 integrin is upregulated and involved in the medical condition's pathological mechanism, comprising administering to the subject the compound or pharmaceutically acceptable salts, esters, solvates, polymorphs or modified forms thereof according to claim 1.

18. The method of claim 17, wherein the medical condition is selected from cancer, infections, fibrosis, cornea dysfunctions, interstitial lung disease, thrombosis, myocardial infarction, coronary myocardial disease, arteriosclerosis, osteoporosis, inflammation, psoriasis and open wounds.

19. The method of claim 17, wherein the medical condition to be treated is cancer selected from oral squamous carcinoma, laryngeal squamous cell carcinoma, oropharyngeal squamous cell carcinoma, nasopharyngeal squamous cell carcinoma, hypopharyngeal squamous cell carcinoma, colon cancer, ovarian carcinoma, non-small cell lung cancer (NSCLC), prostate cancer, lymph node metastasis and gastric cancer, viral infections caused by a virus selected from Foot-and-Mouth-Disease Virus, human parechovirus 1 and coxsackievirus A9, or fibrosis selected from pulmonary fibrosis, cystic fibrosis, idiopathic pulmonary fibrosis, endomyocardial fibrosis, Crohn's disease, and arthofibrosis.

20. The method of claim 18, wherein the medical condition is virus infection.

21. A process for preparing the compound or pharmaceutically acceptable salts, esters, solvates, polymorphs or modified forms thereof according to claim 1, wherein the process includes a first step of generating a linear precursor molecule using Fmoc-based solid phase peptide synthesis techniques, followed by a second step, wherein the linear precursor molecule is cyclized to yield a compound of general formula (I), which optionally includes a further step of modifying the compound of general formula (I) to yield a compound of general formula (II).

22. A method of performing diagnostic imaging in a subject, the method comprising administering to the subject the compound or pharmaceutically acceptable salts, esters, solvates, polymorphs or modified forms thereof according to claim 1, and subjecting the subject to a diagnostic imaging method, wherein the method of diagnostic imaging is performed using one of fluorescence labelling, positron emission tomography (PET), single-photon emission computed tomography (SPECT), optical imaging or magnetic resonance imaging (MRI).

23. A method of performing diagnostic imaging in a subject, the method comprising administering to the subject the pharmaceutical composition according to claim 10, and subjecting the subject to a diagnostic imaging method, wherein the method of diagnostic imaging is performed using one of fluorescence labelling, positron emission tomography (PET), single-photon emission computed tomography (SPECT), optical imaging, or magnetic resonance imaging (MRI).

24. A method of performing diagnostic imaging in a subject having been previously administered the compound or pharmaceutically acceptable salt, ester, solvate, polymorph or modified form thereof according to claim 1, the method comprising, subjecting the subject to a diagnostic imaging method, wherein the method of diagnostic imaging is performed using one of fluorescence labelling, positron emission tomography (PET), single-photon emission computed tomography (SPECT), optical imaging, or magnetic resonance imaging (MRI).

* * * * *